US 7,491,356 B2

(12) United States Patent
Heikkila

(10) Patent No.: US 7,491,356 B2
(45) Date of Patent: Feb. 17, 2009

(54) EXTRUSION METHOD FORMING AN ENHANCED PROPERTY METAL POLYMER COMPOSITE

(75) Inventor: Kurt E. Heikkila, Marine on St. Croix, MN (US)

(73) Assignee: Tundra Composites LLC, White Bear Lake, MN (US)

( * ) Notice: Subject to any disclaimer, the term of this patent is extended or adjusted under 35 U.S.C. 154(b) by 712 days.

(21) Appl. No.: 10/988,193

(22) Filed: Nov. 12, 2004

(65) Prior Publication Data

US 2006/0055077 A1 Mar. 16, 2006

Related U.S. Application Data

(60) Provisional application No. 60/571,456, filed on May 14, 2004, provisional application No. 60/520,507, filed on Nov. 14, 2003.

(51) Int. Cl.
*B29C 70/58* (2006.01)
(52) U.S. Cl. ............. 264/173.16; 264/211; 264/328.18; 264/349
(58) Field of Classification Search ............ 264/173.16, 264/211, 328.18, 349
See application file for complete search history.

(56) References Cited

U.S. PATENT DOCUMENTS

| | | | |
|---|---|---|---|
| 2,748,099 A | 5/1956 | Bruner et al. | |
| 3,895,143 A | 7/1975 | Tarlow | |
| 3,918,141 A | 11/1975 | Pepper et al. | |
| 4,224,267 A | 9/1980 | Lugosi et al. | |
| 4,740,538 A | 4/1988 | Sekutowski | |
| 4,780,981 A | 11/1988 | Hayward et al. | |
| 4,891,399 A | 1/1990 | Ohkawa et al. | |
| 4,949,645 A | 8/1990 | Hayward et al. | |
| 5,019,311 A | 5/1991 | Koslow | |
| 5,026,748 A | 6/1991 | Adams et al. | |
| 5,073,320 A * | 12/1991 | Sterzel ................ | 264/101 |
| 5,130,342 A | 7/1992 | McAllister et al. | |
| 5,147,722 A | 9/1992 | Koslow | |
| 5,237,930 A | 8/1993 | Bélanger et al. | |
| 5,278,219 A | 1/1994 | Lilley et al. | |
| 5,289,997 A | 3/1994 | Harris | |
| 5,373,047 A | 12/1994 | Schnelle et al. | |
| 5,378,407 A | 1/1995 | Chandler et al. | |
| 5,399,187 A | 3/1995 | Mravic et al. | |
| 5,548,125 A | 8/1996 | Sandbank | |
| 5,594,186 A | 1/1997 | Krause et al. | |
| 5,786,416 A | 7/1998 | Gardner et al. | |
| 5,877,437 A | 3/1999 | Oltrogge | |
| 6,048,379 A | 4/2000 | Bray et al. | |
| 6,074,576 A | 6/2000 | Zhao et al. | |
| 6,090,313 A | 7/2000 | Zhao | |
| 6,270,549 B1 | 8/2001 | Amick | |
| 6,364,422 B1 | 4/2002 | Sakaki et al. | |
| 6,413,626 B1 | 7/2002 | Wollner | |
| 6,457,417 B1 | 10/2002 | Beal | |
| 6,517,774 B1 | 2/2003 | Bray et al. | |
| 6,562,290 B2 | 5/2003 | Meinhardt et al. | |
| 6,576,697 B1 | 6/2003 | Brown, Jr. | |
| 6,740,260 B2 | 5/2004 | McCord | |
| 6,815,066 B2 | 11/2004 | Elliott | |
| 6,916,354 B2 | 7/2005 | Elliott | |
| 6,981,996 B2 | 1/2006 | Shaner et al. | |
| 7,204,191 B2 | 4/2007 | Wiley et al. | |
| 7,232,473 B2 | 6/2007 | Elliott | |
| 2002/0124759 A1 | 9/2002 | Amick | |
| 2002/0195738 A1* | 12/2002 | Norquist et al. ........ | 264/173.16 |
| 2003/0027005 A1 | 2/2003 | Elliott | |
| 2003/0069344 A1 | 4/2003 | Nishikawa et al. | |
| 2003/0130418 A1 | 7/2003 | Hamilton et al. | |
| 2003/0146538 A1* | 8/2003 | Sambrook et al. ........... | 264/211 |
| 2003/0161751 A1 | 8/2003 | Elliott | |
| 2003/0164063 A1 | 9/2003 | Elliott | |
| 2004/0177720 A1 | 9/2004 | Shaner et al. | |
| 2005/0005807 A1 | 1/2005 | Wiley et al. | |
| 2005/0043112 A1 | 2/2005 | Stevens et al. | |
| 2005/0062332 A1 | 3/2005 | Amyot et al. | |
| 2005/0188879 A1 | 9/2005 | Wiley et al. | |
| 2005/0258404 A1 | 11/2005 | McCord | |
| 2006/0075919 A1 | 4/2006 | Wiley et al. | |
| 2006/0102041 A1 | 5/2006 | Wiley et al. | |
| 2006/0118211 A1 | 6/2006 | Elliott | |

FOREIGN PATENT DOCUMENTS

| | | |
|---|---|---|
| GB | 2 179 664 A | 3/1987 |
| JP | 63 273 664 | 11/1988 |
| JP | 2001-041290 | 2/2001 |
| JP | 2001-349381 | 12/2001 |
| WO | WO 93/05101 | 3/1993 |
| WO | WO 98/00462 | 1/1998 |
| WO | WO 02/086347 | 10/2002 |
| WO | WO 2005/012408 A2 | 2/2005 |

OTHER PUBLICATIONS

Arkles, B., "Gelest Silane Coupling Agents: Connecting Across Boundaries," *Gelest, Inc.*, Cover Page, pp. 1-20 (© 2003).
Cheney, R., "Production of Tungsten, Molybdenum, and Carbide Powders," *GTE Products Corp.*, pp. 152-159 (Date Unknown).
DePass, D. "Getting the lead out: Alliant's 'green' bullet," *Star Tribune*, http://www.startribune.com/viewers/story.php?template=print_a&story=4075320, 3 pages (Published Sep. 3, 2003).
"Dyneom™ Fluorothermoplastics Product Information," *Dyneon LLC ( A 3M Company)*, 2 pages (Dec. 2000).
"Dyneon™ Fluoroelastomers Processing Fluoroelastomers," *Dyneon LLC ( A 3M Company)*, pp. 1-8 (Jan. 2001).
"Dyneon™ THV Fluorothermoplastics Injection Molding Guidelines," *Dyneon LLC ( A 3M Company)*, 2 pages (Apr. 2001).
"Dyneon™ Fluorothermoplastics FEP X 6301, FEP X 6303 and FEP X 6307," *Dyneon LLC ( A 3M Company)*, 2 pages (Aug. 2001).
"Dyneon™ Fluorothermoplastics THV220A," *Dyneon LLC ( A 3M Company)*, 2 pages (Aug. 2001).

(Continued)

*Primary Examiner*—Robert B Davis
(74) *Attorney, Agent, or Firm*—Merchant & Gould P.C.

(57) ABSTRACT

The invention relates to an extrusion method and to an extrudable metal polymer composite having increased density, improved viscoelastic properties, malleability and ductility and thermoplastic extrusion or injection molding properties.

42 Claims, 7 Drawing Sheets

OTHER PUBLICATIONS

"Dyneon™ Fluoroplastics Product Comparison Guide," *Dyneon LLC (A 3M Company)* 7 pages (Jun. 2003).

"Ecomass® Compounds Product Data Sheet PEM-01-01-110-LTS," *PolyOne Corporation*, 1 page (Apr. 26, 2002).

"Ecomass® Compounds Product Data Sheet PEM-07-01-090-LTS," *PolyOne Corporation*, 1 page (Apr. 26, 2002).

"Ken-React® Reference Manual Titanate, Zirconate and Aluminate Coupling Agents," *Kenrich Petrochemicals, Inc.*, 8 pages (Date Unknown).

Shedd, K. "Tungsten," *U.S. Geological Survey Minerals Yearbook*, 16 pages (1999).

"The Nontoxic Alternative to Lead—Nontoxic High Density Compounds," *MASS®*, 2 pages (Sep. 12, 2003).

"The Nontoxic Alternative to Lead—Specifications," *MASS®*, 2 pages (Date Unknown).

Wadud, S., "Time-Temperature Superposition Using DMA Creep Data," *TA Instruments, Inc.*, pp. 1-4 (Date Unknown).

"Lead Free Weight Suppliers," Materials from web sites of suppliers of auto wheel weights, 2 pages (Jul. 2005).

"Steel Wheel Weights," Materials from web sites of suppliers of auto wheel weights, 1 page (Date Printed Jan. 20, 2006).

"Zinc Wheel Weights," Materials from web sites of suppliers of auto wheel weights, 1 page (Date Printed Jan. 20, 2006).

Search Report for PCT/US 2004/037931 mailed Feb. 23, 2005.

Search Report for PCT/US 2004/037931 mailed May 25, 2005.

\* cited by examiner

EXTRUSION METHOD FORMING AN ENHANCED PROPERTY METAL POLYMER COMPOSITE

RELATED APPLICATION

This application claims priority under 35 U.S.C. §119(e) to U.S. provisional applications Ser. No. 60/520,507, filed on Nov. 14, 2003 and Ser. No. 60/571,456 filed on May 14, 2004, both hereby incorporated by reference herein.

FIELD OF THE INVENTION

The invention relates to a method of extruding an extrudable enhanced property metal polymer composite by novel interactions of the components. The method can be used to extrude the composite material into useful shapes. The extruded high density metal polymer composite materials are not simple admixtures, but obtain enhanced chemical, electrical and mechanical properties from an extrusion of a unique combination of a metal particulate and polymer material matrix that optimizes the properties of the composite through blending the combined polymer and metal materials.

BACKGROUND OF THE INVENTION

High density materials have been made for many years. Lead has been commonly used in applications requiring a high density material. Applications of high density materials include shotgun pellets, other ballistic projectiles, fishing lures, fishing weights, wheel weights and other high density applications. As an example, lead has also been used in applications requiring properties other than density including in radiation shielding because of its resistance to $\alpha$, $\beta$ and $\gamma$ radiation, EMI and malleability characteristics. Press-on fishing weights made of lead allow the user to easily pinch the weight onto a fishing line without tools or great difficulty. In the case of shotgun pellets, or other ballistic projectiles, lead offers the required density, penetrating force and malleability to achieve great accuracy and minimum gun barrel wear. Lead has been a primary choice of both hunting and military applications. Many jurisdictions in the United States and elsewhere have seriously considered bans on the sale and use of lead shot and lead sinkers due to increasing concentrations of lead in lakes and resulting mortality in natural populations. Other high-density materials such as depleted uranium have been proposed and implemented.

Composite materials have been suggested as a replacement for lead and other high-density materials. Composite materials have been made for many years by combining generally two dissimilar materials to obtain beneficial properties from both. A true composite is unique because the interaction of the materials provides the best properties of both components. Many types of composite materials are known and are not simple admixtures. Generally, the art recognizes that combining metals of certain types and at proportions that form an alloy provides unique properties in metal/metal alloy materials. Metal/ceramic composites have been made typically involving combining metal particulate or fiber with clay materials that can be fired into a metal/ceramic composite.

Combining typically a thermoplastic or thermoset polymer phase with a reinforcing powder or fiber produces a range of filled materials and, under the correct conditions, can form a true polymer composite. A filled polymer, with the additive as a filler, cannot display composite properties. A filler material typically is comprised of inorganic materials that act as either pigments or extenders for the polymer systems. A vast variety of fiber-reinforced composites have been made typically to obtain fiber reinforcement properties to improve the mechanical properties of the polymer in a unique composite.

Metal polymer admixtures in which a finely divided metallic material, a metal powder or fiber is dispersed in a polymer have been suggested. One subset of filled polymer materials is metal polymer admixtures in which a metallic material, a metal particulate or fiber is dispersed in a polymer. The vast majority of these materials are admixtures and are not true composites. Admixtures are typically easily separable into the constituent parts and display the properties of the components. A true composite resists separation and displays enhanced properties of the input materials. A true composite does not display the properties of the individual components. Tarlow, U.S. Pat. No. 3,895,143, teaches a sheet material comprising elastomer latex that includes dispersed inorganic fibers and finely divided metallic particles. Bruner et al., U.S. Pat. No. 2,748,099, teach a nylon material containing copper, aluminum or graphite for the purpose of modifying the thermal or electrical properties of the material, but not the density of the admixture. Sandbank, U.S. Pat. No. 5,548,125, teaches a clothing article comprising a flexible polymer with a relatively small volume percent of tungsten for the purpose of obtaining radiation shielding. Belanger et al., U.S. Pat. No. 5,237,930, disclose practice ammunition containing copper powder and a thermoplastic polymer, typically a nylon material. Epson Corporation, JP 63-273664 A shows a polyamide containing metal silicate glass fiber, tight knit whiskers and other materials as a metal containing composite. Bray et al., U.S. Pat. Nos. 6,048,379 and 6,517,774, disclose an attempt to produce tungsten polymer composite materials. The patent disclosures combine tungsten powder having a particle size less than 10 microns, optionally with other components and a polymer or a metal fiber. The materials sold by the Bray et al. assignee and the materials disclosed in the patent do not attain a density greater than 10.0 gm-cm$^{-3}$.

While a substantial amount of work has been done regarding composite materials generally, high density metal composite materials have not been obtained having a density greater than 10 grams-cm$^{-3}$, where density is a single measurement to illustrate the composite property. Increasing the density of these materials introduces unique mechanical properties into the composite and, when used, obtains properties that are not present in the lower density composite materials. A substantial need exists for an extrudable material that has high density, low toxicity, and improved properties in terms of electrical/magnetic properties, malleability, thermal processability, particularly using existing thermal processing equipment, and viscoelastic properties.

BRIEF DESCRIPTION OF THE INVENTION

The invention relates to an extrusion method and an extrudable metal polymer composite material having improved properties with respect to prior art materials. The material of the invention, through a selection of metal particle size distribution, polymer and processing conditions, attains improved density or other properties through minimization of the polymer filled excluded volume of the composite. The resulting composite materials exceed the prior art composites in terms of density, reduced toxicity, improved malleability, improved ductility, improved viscoelastic properties (such as tensile modulus, storage modulus, elastic-plastic deformation and others) electrical/magnetic properties, and machine molding properties and substantially reduced wear on processing equipment. We have produced true composites and can obtain viscoelastic properties. We have produced a composite by using an interfacial modifier to improve the association of the particulate with the polymer. We have found that the composite materials of the invention can have a designed level of density, mechanical properties, or electrical/magnetic properties from careful composition blending. The novel viscoelastic properties make the materials useful in a variety of uses not filled by composites and provides a material easily made and formed into useful shapes. We have found that density and polymer viscoelasticity measured as elongation are useful properties and useful predictive parameters of a true composite in this technology. In the production of useful enhanced properties, the packing of the selected particle size and distribution and the selection of the particulate or mixed metal particulate, will obtain the enhanced properties. As such density can be used as a predictor of the other useful property enhancement. The invention relates to an extruded enhanced metal polymer composite material having improved properties with respect to prior art materials. Single metal and mixed metal composites can be tailored for increasing a variety of properties including but not limited to density, color, magnetism, thermal conductivity, electrical conductivity and other physical properties. The use of compositions further comprising an interfacial modifier demonstrates improved utilization of material properties and improved performance such as elongation and other properties. Preferred composites can be combined with one or more polymers of a given molecular weight distribution and one or more metal particulates with a given distribution to obtain unique composites. Briefly, the metal polymer composites of the invention can be extruded into a high-density material comprising a high-density metal particulate of defined particle size and size distribution, a polymer, and optionally an interfacial modifier material. In one embodiment of the invention, a metal particulate composite can be made by a careful selection of metal particulate size and distribution. In a further embodiment of the invention, a metal thermoplastic composite can be made.

In another embodiment, a interfacial modifier is used to ensure that the proportions of metal particulate and polymer obtain the minimum excluded volume filled with polymer, the highest particulate packing densities, the maximize polymer composite material and obtain the maximum utilization of materials. The particle shape, size and distribution of the metal component is controlled to maximize the extruded composite density and other properties. The high-density materials of the invention can contain about 0.005 to 1% of a pigments, dye or other fluorescent material or other ingredients to modify the visual appearance of the materials. Mixed metal or alloy metal composites can be used to tailor densities for specific uses. Aforementioned properties include but are not limited to density, thermal properties such as conductivity, magnetic properties, electrical properties such as conductivity, color, etc. Preferred higher density metal polymer materials can also be combined with one or more polymers and one or more metal particulates to obtain unique composites. A secondary metal can be combined with a metal of high density. A composite can comprise a variety of different combinations of metals and polymers. The metal particulate can contain two metal particulates of different metals, each metal having a relatively high density. In another embodiment, the metal particulate can comprise a metal particulate of high density and a secondary metal. Other useful metals of this disclosure relates to a metal that, by itself, cannot achieve a density greater than 10 grams-$cm^{-3}$ in the composite material, but can provide useful properties to the composite as a whole. Such properties can include electrical properties, magnetic properties, physical properties, including heat conductivity, acoustical shielding, etc. Examples of such secondary metals include, but are not limited to, iron copper, nickel, cobalt, bismuth, tin, cadmium and zinc. The materials of the invention permit the design engineer the flexibility to tailor the extrusion process of the invention and the extruded composite of the invention to end uses and avoid the use of toxic or radioactive materials unless desired. Lead or depleted uranium are no longer needed in their typical applications now that dense composites are available. In other applications where some tailored level of toxicity or radiation is needed, the composites of the invention can be used successfully.

The compositions of the invention can also contain other additives to modify the visual appearance of the materials such as a visual indicator, fluorescent marker, dye, or pigment. The composites of the invention comprise about 45 to 95 volume-% metal or about 45 to 96 volume-% metal, and about 5 to 53 volume-% polymer or 4 to 53 volume-% polymer in the composite. In this disclosure we rely on density as one important property that can be tailored in the composite, however other properties can also be designed as well.

Enhanced property metal polymer composites can be made by melt forming, preferable extruding, an extrudable composite. In the composite, the metal particulate is obtained at the highest possible packing by a careful selection of particle size and size distribution. The excluded volume in the particulate are substantially completely occupied by the polymer without reducing the composite density. Using a carefully selected finely divided metal, packing the particulate and combining the particulate with just sufficient polymer such that only the excluded volume (the space left after packing the particle distribution) of the particulate is filled can optimize the high density of the composite material. A metal particulate, or metal particulate blend, is selected having an absolute density of metal greater than about 4 grams-$cm^{-3}$, greater than 10 grams-$cm^{-3}$ and often greater than 16 gm-$cm^{-3}$. The particulate has a selected particle size and size distribution that is combined with a polymer selected for compatibility and increased density and processability. As the metal particulate and the polymer component increase in density, the composite material increases in density. The ultimate composite density is largely controlled by efficiency in packing of the metal particulate in the composite and the associated efficiency in filling the unoccupied voids in the densely packed particulate with high density polymer material. The interfacial modifier can aid in closely associating the metal particulate and polymer to maximize density. A true composite is obtained by carefully processing the combined polymer and polymer particulate until density reaches a level showing that using an interfacial modifier to promote composite formation results in enhanced property development and high density. In this disclosure, we rely on density as one important property that can be tailored in the composite but other useful properties can be designed into the composite.

A composite is more than a simple admixture. A composite is defined as a combination of two or more substances intermingled with various percentages of composition, in which each component retains its essential original properties. A controlled combination of separate materials results in properties that are superior to those of its constituents. In a simple admixture the mixed material have little interaction and little property enhancement. One of the materials is chosen to increase stiffness, strength or density. Atoms and molecules can form bonds with other atoms or molecules using a number of mechanisms. Such bonding can occur between the electron cloud of an atom or molecular surfaces including molecular-molecular interactions, atom-molecular interactions and atom-atom interactions. Each bonding mechanism involves characteristic forces and dimensions between the atomic centers even in molecular molecular interactions. The important aspect of such bonding force is strength, the variation of bonding strength over distance and directionality. The major forces in such bonding include ionic bonding, covalent bonding and the van der Waals' (VDW) types of bonding. Ionic radii and bonding occur in ionic species such as $Na^+Cl^-$, $Li^+F^-$. Such ionic species form ionic bonds between the atomic centers. Such bonding is substantial, often substantially greater than 100 $kJ\text{-}mol^{-1}$ often greater than 250 $kJ\text{-}mol^{-1}$. Further, the interatomic distance for ionic radii tend to be small and on the order of 1-3 Å. Covalent bonding results from the overlap of electron clouds surrounding atoms forming a direct covalent bond between atomic centers. The covalent bond strengths are substantial, are roughly equivalent to ionic bonding and tend to have somewhat smaller interatomic distances.

The varied types of van der Waals' forces are different than covalent and ionic bonding. These van der Waals' forces tend to be forces between molecules, not between atomic centers. The van der Waals' forces are typically divided into three types of forces including dipole-dipole forces, dispersion forces and hydrogen bonding. Dipole-dipole forces are a van der Waals' force arising from temporary or permanent variations in the amount or distribution of charge on a molecule.

Summary of Chemical Forces and Interactions

| Type of Interaction | Strength | Bond Nature | Strength Proportional to: |
|---|---|---|---|
| Covalent bond | Very strong | Comparatively long range | $r^{-1}$ |
| Ionic bond | Very strong | Comparatively long range | $r^{-1}$ |
| Ion-dipole | Strong | Short range | $r^{-2}$ |
| VDW Dipole-dipole | Moderately strong | Short range | $r^{-3}$ |
| VDW Ion-induced dipole | Weak | Very short range | $r^{-4}$ |
| VDW Dipole-induced dipole | Very weak | Extremely short range | $r^{-6}$ |
| VDW London dispersion forces | Very weak[a] | Extremely short range | $r^{-6}$ |

[a]Since VDW London forces increase with increasing size and there is no limit to the size of molecules, these forces can become rather large. In general, however, they are very weak.

Dipole structures arise by the separation of charges on a molecule creating a generally or partially positive and a generally or partially negative opposite end. The forces arise from electrostatic interaction between the molecule negative and positive regions. Hydrogen bonding is a dipole-dipole interaction between a hydrogen atom and an electronegative region in a molecule, typically comprising an oxygen, fluorine, nitrogen or other relatively electronegative (compared to H) site. These atoms attain a dipole negative charge attracting a dipole-dipole interaction with a hydrogen atom having a positive charge. Dispersion force is the van der Waals' force existing between substantially non-polar uncharged molecules. While this force occurs in non-polar molecules, the force arises from the movement of electrons within the molecule. Because of the rapidity of motion within the electron cloud, the non-polar molecule attains a small but meaningful instantaneous charge as electron movement causes a temporary change in the polarization of the molecule. These minor fluctuations in charge result in the dispersion portion of the van der Waals' force.

Such VDW forces, because of the nature of the dipole or the fluctuating polarization of the molecule, tend to be low in bond strength, typically 50 $kJ\,mol^{-1}$ or less. Further, the range at which the force becomes attractive is also substantially greater than ionic or covalent bonding and tends to be about 3-10 Å.

In the van der Waals composite materials of this invention, we have found that the unique combination of metal particles, the varying particle size of the metal component, the interfacially modification of the interaction between the particulate and the polymer, result in the creation of a unique van der Waals' bonding. The van der Waals' forces arise between metal atoms/crystals in the particulate and are created by the combination of particle size, polymer and interfacial modifiers in the metal/polymer composite. In the past, materials that are characterized as "composite" have merely comprised a polymer filled with particulate with little or no van der Waals' interaction between the particulate filler material. In the invention, the interaction between the selection of particle size, distribution, polymer, and optional interfacial modifier enables the particulate to achieve an intermolecular distance that creates a substantial van der Waals' bond strength. The prior art materials having little viscoelastic properties, do not achieve a true composite structure. This leads us to conclude that this intermolecular distance is not attained in the prior art. In the discussion above, the term "molecule" can be used to relate to a particle of metal, a particle comprising metal crystal or an amorphous metal aggregate, other molecular or atomic units or sub-units of metal or metal mixtures. In the composites of the invention, the van der Waals' forces occur between collections of metal atoms that act as "molecules" in the form of crystals or other metal atom aggregates.

The composite of the invention is characterized by a composite having intermolecular forces between metal particulates that are in the range of van der Waals' strength, i.e., between about 5 and about 30 $kJ\text{-}mol^{-1}$ and a bond dimension of 3-10 Å.

Most composites have two constituent materials: a binder or matrix, and reinforcement. The reinforcement is usually much stronger and stiffer than the matrix, and gives the composite its good properties. The matrix holds the reinforcements in an orderly high density pattern. Because the reinforcements may be discontinuous, the matrix may also help to transfer load among the reinforcements. Processing can aids in the mixing and filling of the reinforcement metal. To aid in the mixture, an interfacial modifier can help to overcome the forces that prevent the matrix from forming a substantially continuous phase of the composite. The composite properties arise from the intimate association obtained by use of careful processing and manufacture. Composites that demonstrate viscoelastic properties are possible with certain polymers without an interfacial modifier. We believe an interfacial modifier is an organic material that provides an exterior coating on the particulate promoting the close association of polymer and particulate. The modifier is used in an amount of about 0.005 to 3 wt. %.

For the purpose of this disclosure, the term "metal" relates to metal in an oxidation state, approximately 0, with up to 25 wt.-% or about 0.001 to 10 wt.-% as an oxide or a metal or non-metal contaminant, not in association with ionic, covalent or chelating (complexing) agents. For the purpose of this disclosure, the term "particulate" typically refers to a material made into a product having a particle size greater than 10 microns (a particle size greater than about 10 microns means that a small portion of the particulate is less than 10 microns, in fact, less than 10 wt.-% of the particulate and often less than 5 wt.-% of the particulate is less than 10 microns. A particulate is chosen containing at least some particulate in the size range of 10 to 100 microns and 100 to 4000 microns. In a packed state, this particulate has an excluded volume of about 13 to 60 vol.-% or about 40 to 60 vol.-%. In this invention, the particulate sources, can comprise two three or more particulates, in a blend of metals of differing chemical and physical nature.

Typically, the composite materials of the invention are manufactured using melt extrusion processing (compression and injection molding can also be used) and are also utilized in product formation using melt processing. Typically, in the manufacturing of the high density materials of the invention, a finely divided metal material of correctly selected particle size and size distribution is combined under conditions of heat and temperature with a typically thermoplastic polymer material, are processed until the material attains a maximum density. The density can be at least 4 gm-cm$^{-3}$, greater than 7 gm-cm$^{-3}$, greater than 10 gm-cm$^{-3}$, greater than 11 gm-cm$^{-3}$, preferably greater than 13 gm-cm$^{-3}$, more preferably greater than 16 gm-cm$^{-3}$ with improved mechanical, electrical, magnetic or catalytic properties indicating true composite formation. These materials and combination of materials can be used as solid state electrochemical (e.g. battery) and semiconductor structures. Alternatively, in the manufacture of the material, the metal or the thermoplastic polymer can be blended with a interfacially modifying (interfacial modifier) agents and the modified materials can then be melt processed into the material. The interfacial modifier can make the surface of the particulate more compatible with the polymer. Once the material attains a sufficient density and other properties, the material can be extruded directly into a final product or into a pellet, chip, wafer or other easily processed production raw material. The final product or intermediate chip or pellet can be made extrusion-processing techniques. In the manufacture of useful products with the composites of the invention, the manufactured composite can be obtained in appropriate amounts, subjected to heat and pressure, typically in extruder equipment and then either injection molded, compression molded or extruded into an appropriate useful shape having the correct amount of materials in the appropriate physical configuration. In the appropriate product design, during composite manufacture or during product manufacture, a pigment or other dye material can be added to the processing equipment. One advantage of this material is that an inorganic dye or pigment can be co-processed resulting in a material that needs no exterior painting or coating to obtain an attractive or decorative appearance. The pigments can be included in the polymer blend, can be uniformly distributed throughout the material and can result in a surface that cannot chip, scar or lose its decorative appearance. One useful pigment material comprises titanium dioxide (TiO$_2$). This material is extremely non-toxic, is a bright white, finely divided metallic particulate that can be easily combined with either metal particulates and/or polymer composites to enhance the density of the composite material and to provide a white hue to the ultimate composite material.

We have further found tat a bimetallic blend or a blend of three or more metal particulates can, obtain important composite properties from the blended metals in a polymer composite structure. For example, a tungsten composite or other high density metal can be blended with a second metal that provides to the relatively stable, non-toxic tungsten material, additional properties including a low degree of radiation in the form of alpha, beta or gamma particles, a low degree of desired cytotoxicity, a change in appearance or other beneficial properties. One advantage of a bimetallic composite is obtained by careful selection of proportions resulting in a tailored density for a particular end use. For example. a copper/tungsten composite can be produced having a theoretical density, for example, with a fluoropolyrmer or fluorocarbon that can range from 7 gm-cm$^{-3}$ through 11.4 gm-cm$^{-3}$. For example, a tantalum/tungsten composite can be produced having a theoretical density, for example, with a (fluoropolymer that can range from 11 gm-cm$^{-3}$ through 12.2 gm-cm$^{-3}$. Alternatively, for other applications, an iridium/tungsten composite can be manufactured that, with a fluoropolymer or fluoropolymer elastomer, can have a density that ranges front about 12 to about 13.2 gm-cm$^{-3}$. Such composites each can have unique or special properties. The extrudable material having high density that can be extruded into useful shapes include a material having a composite density of about 4 to 17 gm-cm$^{-3}$, preferably about 6 to 16 gm-cm$^{-3}$, at an extruded shear rate, in common processing equipment that ranges from about 1 sec$^{-1}$ to about 500 sec$^{-1}$, preferably about 10 to about 250 sec$^{-1}$ at a temperature of greater than about 100° C., and preferably 150 to 180° C., although for some materials it may be more preferable to process at temperatures above 180° C. The tensile strength can be about 0.2 to 60 MPa, the storage modulus of the composite (G$^1$) ranges from about 300 to about 14,000 MPa, preferably from about 1200 to 14,000 MPa, and most preferably from about 3000 to about 7000 MPa and a tensile modulus of at least 0.2 to 200 MPa. One important characteristic of the extrudable material of the invention relates to the existence of an elastic-plastic deformation and its Poisson ratio. The extruded materials of the invention display an elastic plastic deformation. Under a stress that causes the extruded to elongate, the structure deforms in an elastic mode until it reaches a limit after which it deforms in a plastic mode until it reaches its limit and fails structurally. This property is shown as the elongation at break in which the material elongates under stress by at least 10% before reaching a limit and breaking under continued stress. The preferred material has a Poisson ratio typically less than 0.5 and preferably about 0.1 to about 0.5. Such a Poisson ratio indicates that it can be extruded with little elastic relaxation during processing.

DETAILED DESCRIPTION OF THE INVENTION

Figure 1:
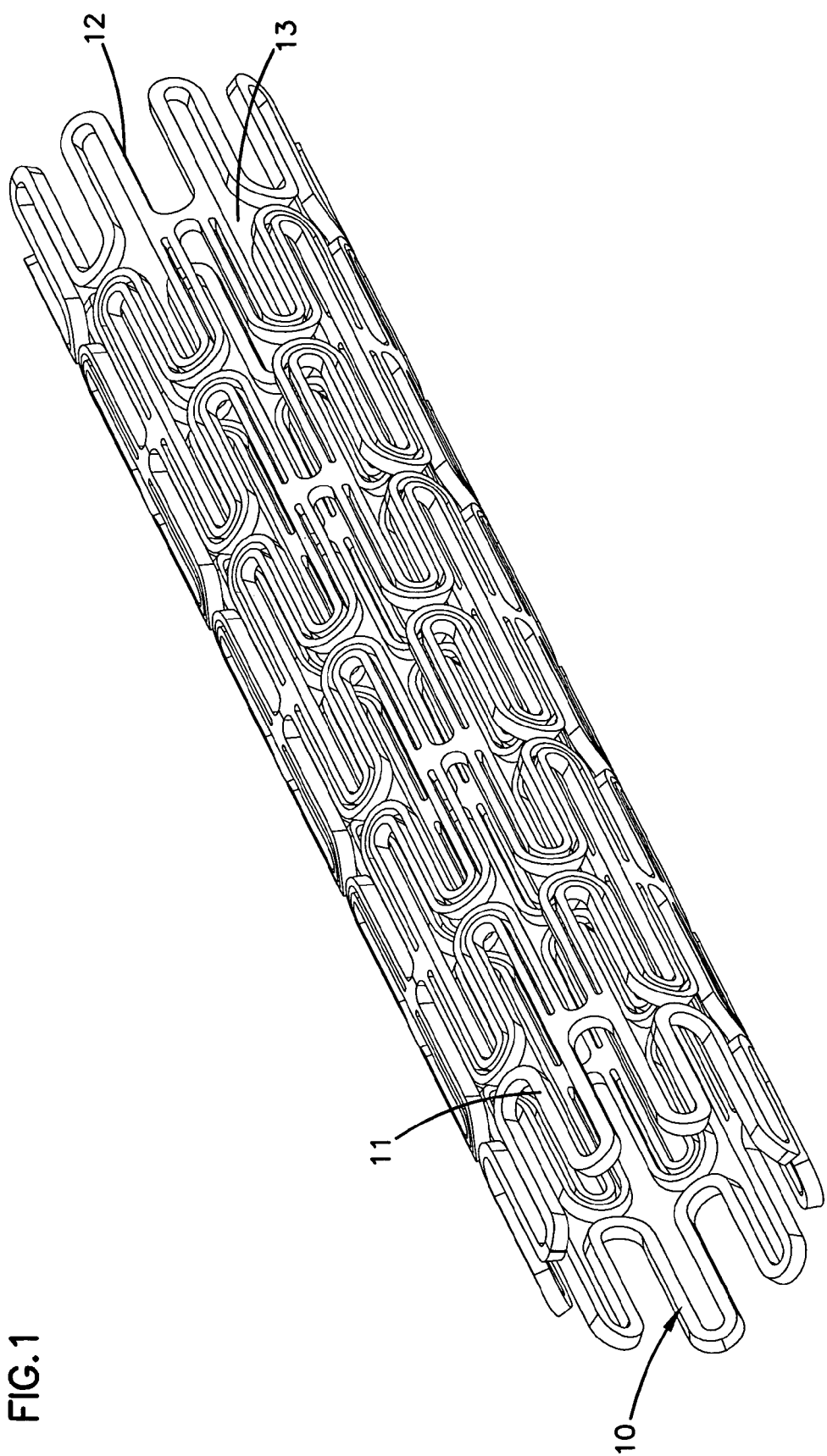
FIG. 1 is a molded article made from the material of the invention. As an example of a structure that can be molded using the various methods described herein the stent is an example of an article with a flexible structure that obtains utility from the metal polymer composite of the invention.

The invention relates to an extrusion process and an extruded metal polymer composite material having enhanced or improved properties with respect to prior art materials. Single metal and mixed metal composites can be tailored for novel properties including density, color, magnetism, thermal conductivity, electrical conductivity and other physical properties. The use of compositions further comprising an interfacial modifier demonstrates improved utilization of material properties and improved performance. Preferred composites can be combined with one or more polymers of a given molecular weight distribution and one or more metal particulates with a given distribution to obtain unique composites. The invention relates to a family of composite materials having composite characteristics that exceed the density and greatly improves viscoelastic properties of prior art metal composites. The materials can be used in applications requiring high-density properties, viscoelastic character, malleability, ductility, formability and extrusion molding properties. The invention specifically provides high-density materials comprising a high-density metal particulate or particulate blends, a polymer phase and when needed, an interfacial modifier that permits the polymer and metal particulate to interact to form a composite with desired nature and degree of properties and to attain the maximum density possible. Such materials obtain physical properties in excess of prior art materials including density, storage modulus color, magnetism, thermal conductivity, electrical conductivity and other physical property improvements without toxicity or residual radiation characteristic of lead or depleted uranium, respectively unless needed in a specific application. The material of the invention permit the design engineer the flexibility to tailor the composite to end uses and avoid the use of toxic or radioactive materials unless desired. Lead or depleted uranium are no longer needed in their typical applications.

The composite materials of the invention combine a metal particulate at a maximum tap density leaving a excluded volume and a polymer material substantially occupying the excluded volume, but no more to obtain the highest possible density from the composite composition. Tap density (ASTM B527-93) relates to how well the material is packed. Packing affects the excluded volume and a volume component that is included in the density calculation. The particle size and size distribution of the particulate appears to be important in attaining the highest density composite materials of the invention. We have found that the minimum useful particle size of the particulate is about 10 microns. Below 10 microns, the processability of the material as a homogeneous mixture is reduced and prevents close association between the metal particulate and the polymer. Further, the small particle size tends to promote the incorporation of voids within the composite. Particulate or blends greater than 10 microns in size appears to be useful in attaining close association between the metal particulate and the polymeric material. We have also found that it is important to include a broad range of particulate. The metal particulate contain at least an effective amount of at least one particulate having a particle size greater than 10 microns (less than 10 wt.-% often less than 5 wt.-% of the particulate is less than 10 microns). The size distribution should include a broad range. This set of broad distributions yield a material that will pack and be readily processable. This particulate distribution should contain at least some particulate (at least 5 wt.-%) in the range of about 10 to 70 microns, the particulate distribution should also contain at least some particulate (at least 5 wt.-%) in the range of about 70 to 250 microns, optionally the particulate can contain some particulate (at least 5 wt.-%) in the range of about 250 to 500 microns and can contain some particulate in the 500+ micron range. We have found that this varied size distribution promotes close packing of the particulate, reduction in the exclusion volume in the polymer and improved particle polymer compatibility. We have found that this distribution of particles having a selected size distribution and an ultimate size greater than 10 microns greatly improves packing density, interfacial modification and ultimate composite formation. This distribution can be normal, Gaussian, log normal or skew normal but must include the desired range of particle sizes. A true composite is obtained by carefully processing the combined polymer and polymer particulate until properties are developed and density reaches a level showing that using an interfacial modifier promotes composite formation fills the excluded volume results in enhanced property development and high density.

The regular, essentially spherical, character of the preferred particles of the invention can be defined by the roughness or roundness of the particle and by its aspect ratio. The aspect ratio of the particles should be less than 1:1.5 and should reflect a substantially circular cross section or spherical particle. The circularity, roundness or roughness of the particle can be measured by a microscopic inspection of the particles in which an automated or manual measurement of roughness can be calculated. In such a measurement, the perimeter of a representative selection of the particulate is selected and the area of the particle cross section is also measured. The roundness of the particle is calculated by the following formula:

$$\text{Circularity} = (\text{perimeter})^2/\text{area}.$$

An ideal spherical particle has a roundness characteristic of about 12.6. This roundness characteristic is unitless parameter of less than about 20, often about 13 to 18. Metal and finely divided metal compositions that can be used in the composites of the invention include, but are not limited to, titanium, chromium, iron, nickel, molybdenum, tin tungsten, cobalt, copper, zinc, cadmium, bismuth, uranium, osmium, iridium, platinum, rhenium, gold, neptunium, plutonium and tantalum. An advantage is that non-toxic or non-radioactive materials can be used as a substitute for lead and depleted uranium where needed. Another advantage of the invention is the ability to create bimetallic or higher composites that use two or more metal materials that cannot naturally form an alloy. A variety of properties can be tailored through a careful selection of metal or a combination of metals and polymer and the toxicity or radioactivity of the materials can be designed into the materials as desired.

We have further found that a blend of two, three or more metals in particulate form can, obtain important composite properties from both metals in a polymer composite structure. For example, a tungsten composite or other high density metal particulate can be blended with a second metal particulate that provides to the relatively stable, non-toxic tungsten material, additional properties including a low degree of radiation in the form of alpha, beta or gamma particles, a low degree of desired cytotoxicity, a change in appearance or other beneficial properties. One advantage of a bimetallic composite is obtained by careful selection of proportions resulting in a tailored density for a particular end use. For example, a tantalum/tungsten composite can be produced having a theoretical density, for example, with a fluoropolymer or fluoropolymer elastomer that can range from 11 gm-$cm^{-3}$ through 12.2 gm-$cm^{-3}$. Alternatively, for other applications, a iridium tungsten composite can be manufactured that, with a fluoropolymer or fluoropolymer elastomer, can have a density that ranges from about 12 gm-$cm^{-3}$ to about 13.2 gm-$cm^{-3}$. Such composites each can have unique or special properties. These composite processes and materials have the unique capacity and property that the composite acts as an alloy composite of two different metals that could not, due to melting point and other processing difficulties, be made into an alloy form without the methods of the invention.

The extrudable composite materials of the invention combine a finely divided metal or metal particulate at a maximum packing density leaving an excluded volume and a polymer material substantially occupying the excluded volume, but no more to obtain the highest possible density from the composite composition. The composite can contain about 50 to 96 or about 80 to 96 vol.-% metal particulate. A variety of metal particulates in the correct size and distribution can be used with density greater than 4, greater than 8, greater than 10 or greater than 13 gm-cm$^{-3}$. The important parameters of the metal particulate material include the fact that no more than 5 wt.-% of the metal particulate is less than 10 microns in diameter. Further, this distribution can be described by Table A, the metal particle having a substantial proportion of particulate falling in the range of 10 to 50 microns, a substantial proportion of a particulate falling in the range of 50 to 350 microns and a substantial proportion of a particulate falling in the range of 350 to 2400 microns. By a substantial proportion, we mean at least 10 wt.-% of the particulate. A more preferred particulate range is as follows: 10 wt.-% 10 to 50 microns, 15 wt.-% 50 to 350 microns, 75 wt.-% 350 to 2400 microns The most preferred particulate range is as follows: 5 wt.-% 10 to 70 microns, 10 wt.-% 70 to 90 microns, 15 wt.-% 90 to 500 microns, 70 wt.-% 500 to 4000 microns. A number of metal particles can be used in the compositions of the invention.

The following are examples of useful metals. Titanium has a symbol Ti, an atomic weight of 47.867 and common valence of 2, 3, 4 (mostly tetravalent). The metal is in Group IVB (4) It is the ninth most abundant element in earth's crust; 0.63% by wt. Reviews: *Gmelin's, Titanium* (8th ed.) 41 (1951); Everhart, *Titanium and Titanium Alloys* (Reinhold, New York, 1954); Brophy et al., *Titanium Bibliography* 1900-1951+ suppl (Washington, 1954); McQuillan & McQuillan, *Titanium* (Butterworth's, London, 1956); Barksdale, *Titanium, Its Occurrence, Chemistry and Technology* (Ronald Press, New York, 2nd ed, 1966); Clark, "Titanium" in *Comprehensive Inorganic Chemistry* vol. 3, J. C. Bailar, Jr. et al., Eds. (Pergamon Press, Oxford, 1973) pp 355-417. The metal is a dark gray, lustrous metal with a mp 1677°, a bp 3277°, and a specific heat (25°) of 5.98 cal/g-atom/° C. The metal forms alloys with aluminum, chromium, cobalt, copper, iron, lead, nickel, tin. The metal can be used as an alloy with copper and iron in titanium bronze, as addition to steel to impart great tensile strength and to aluminum to impart resistance to attack by aqueous salt and by organic acids.

Chromium has a symbol Cr, an atomic weight and number of 51.9961 and 24 and common valences of 1-6. The metal is in Group VIB(6) and is abundant in earth's crust. For a review of chromium and alloys see: *Chromium*, M. J. Udy, Ed., A.C.S. Monograph Series, no. 132 (Reinhold, New York, 1956) vol. 1, 433 pp; vol. 2, 402 pp; C. L. Rollinson, "Chromium, Molybdenum and Tungsten" in *Comprehensive Inorganic Chemistry* vol. 3. Chromium is a steel-gray, lustrous metal; body-centered cubic structure; hard as corundum and less fusible than platinum. Chromium exhibits a mp of 1903±10°, a bp of 2642°, a $d^{20}$ of 7.14, a heat capacity (25°) of 5.58 cal/mol/deg C.°, a heat of fusion of 3.5 kcal/mol, a heat of vaporization of 81.7 kcal/mol (at bp), a $d^{20}$ of 7.19 a specific heat (25° C.) of 23.9 J/mol/deg K and a heat of fusion of 14.6 kJ/mol. Chromium is resistant to common corroding agents, is acid resistant, (i.e.) and reacts with dil HCl, $H_2SO_4$ but not with $HNO_3$. Chromium is useful in chrome steel or chrome-nickel-steel alloys (stainless steel), nonferrous alloys and heat resistant bricks for refractory furnaces. To greatly increase strength, hardness and resistance of metals to abrasion, corrosion and oxidation.

Iron has a symbol Fe, an atomic weight of 55.845, exhibits common valences of 2 and 3 and is in Group VIII(8). Iron is the second most abundant metal in earth's crust after aluminum. See the comprehensive reviews: Feldmann, Schenck in *Ullmanns Encyklopädie der Technischen Chemie* vol. 6 (München-Berlin, 1955) pp 261-407; Nicholls in *Comprehensive Inorganic Chemistry* vol. 3, J. C. Bailar, Jr. et al., Eds. (Pergamon Press, Oxford, 1973) pp 979-1051; W. A. Knepper in *Kirk-Othmer Encyclopedia of Chemical Technology* vol. 13 (Wiley-Interscience, New York, 3rd ed., 1981) pp 735-753. Iron is a silvery-white or gray, soft, ductile, malleable, somewhat magnetic metal. Holds magnetism only after hardening (as alloy steel, e.g., Alnico). Stable in dry air but readily oxidizes in moist air, forming rust. In powder form it is black to gray and can be alloyed with C, Mn, Cr, Ni, and other elements to form steels.

Nickel has a symbol Ni, an atomic weight of 58.6934, a common valence 2 and is in Group VIII(10). Nickel's abundance in earth's crust is 99 ppm. See the comprehensive reviews in *Gmelin's, Nickel* (8th ed.) 57, 5 vols, about 3500 pp (1965-1967); Nicholls in *Comprehensive Inorganic Chemistry* vol. 3, J. C. Bailar, Jr. et al., Eds. (Pergamon Press, Oxford, 1973) pp 1109-1161; J. K. Tien, T. E. Howson in *Kirk-Othmer Encyclopedia of Chemical Technology* vol. 15 (Wiley-Interscience, New York, 3rd ed., 1981) pp 787-801; Nickel is a lustrous white, hard, ferromagnetic metal with face-centered cubic crystals having a mp 1453° and a bp (calc) 2732°. Nickel is stable in air at ordinary temp; burns in oxygen, forming NiO, is not affected by water and decomposes steam at a red heat. Nickel is slowly attacked by dil hydrochloric or sulfuric acid, is readily attacked by nitric acid but is not attacked by fused alkali hydroxides. Nickel can be used for nickel-plating, for various alloys such as Monel metal, stainless steels, heat resistant steels, heat and corrosion resistant alloys, nickel-chrome resistance wire and in alloys for electronic and space applications.

Molybdenum has a symbol Mo an at. wt 95.94, common valences 2,3,4,5,6 and is in Group VIB(6). Molybdenum has an occurrence in the earth's crust of about 1-1.5 ppm. See review of molybdenum in Rollinson, "Chromium, Molybdenum and Tungsten" in *Comprehensive Inorganic Chemistry* vol. 3, J. C. Bailar Jr. et al., Eds. (Pergamon Press, Oxford, 1973) pp 622-623, 700-742; R. Q. Barr in *Kirk-Othmer Encyclopedia of Chemical Technology* vol. 15 (Wiley-Interscience, New York, 3rd ed., 1981) pp 670-682. Molybdenum is a dark-gray or black powder with metallic luster or coherent mass of silver-white color; body-centered cubic structure with a mp 2622° (Worthing), a bp ~4825° a d of 10.28 and a spec heat 5.68 cal/g-atom/deg. Molebdenum is stable at ordinary temp, is oxidized to the trioxide at a red heat and slowly oxidized by steam. Molybdenum is not attacked by water, by dil acids or by conc'd hydrochloric acid and is practically insoluble in alkali hydroxides or fused alkalis. The metal reacts with nitric acid, hot concentrated sulfuric acid, fused potassium chlorate or nitrate. The metal can be used in the form of ferromolybdenum for manufacturing special steels for tools, boiler plate, rifle barrels, propeller shafts, electrical contacts, spark plugs, x-ray tubes and nonferrous alloys. The metal can be used in colloidal form as lubricant additive.

Tin has a symbol of Sn and at. wt 118.710, a common valences of 2 and 4 an is in Group IVA(14) Tin has an occurrence in earth's crust of 6×10$^{-4}$%. The metal of commerce is about 99.8% pure. See the *Monograph*: C. L. Mantell, *Tin: Its Mining, Production, Technology and Applications* (Reinhold, New York, 1949) and W. Germain et al., in *Kirk-Othmer Encyclopedia of Chemical Technology* vol. 23 (Wiley-Interscience, New York, 3rd ed., 1983) pp 18-42. Tin is a silver-white, lustrous, soft, very malleable and ductile metal that is easily powdered. The metal is available in the form of bars, foil, powder, shot, etc. The metal is table in air, but when in powder form it oxidizes, esp in presence of moisture. Tin is chiefly for tin-plating, soldering alloys, babbitt and type metals, manufacture of tin salts, etc.

Tungsten (W) has an atomic weight of 183.84; an atomic number of 74 and is in Group VIB(6). Naturally occurring isotopes are 180 (0.135%); 182 (26.4%); 183 (14.4%); 184 (30.6%); 186 (28.4%); artificial radioactive isotopes are 173-179; 181; 185; 187-189. Tungsten was discovered by C. W. Scheele in 1781 and isolated in 1783 by J. J. and F. de Elhuyar. One of the rarer metals, it comprises about 1.5 ppm of the earth's crust. Chief ores are Wolframite [(Fe,Mn)WO$_4$] and Scheelite (CaWO$_4$) found chiefly in China, Malaya, Mexico, Alaska, South America and Portugal. Scheelite ores mined in the U.S. carry from 0.4-1.0% WO$_3$. Description of isolation processes are found in K. C. Li, C. Y. Wang, *Tungsten*, A.C.S. Monograph Series no. 94 (Reinhold, New York, 3rd ed., 1955) pp 113-269; G. D. Rieck, *Tungsten and Its Compounds* (Pergamon Press, New York, 1967) 154 pp. *Reviews*: Parish, *Advan. Inorg. Chem. Radiochem.* 9, 315-354 (1966); Rollinson, "Chromium, Molybdenum and Tungsten" in *Comprehensive Inorganic Chemistry* Vol. 3, J. C. Bailar, Jr. et al., Eds. (Pergamon Press, Oxford, 1973) pp 623-624, 742-769. Tungsten is a steel-gray to tin-white metal having in crystal form, a body centered cubic structure. Its density is $d_4^{20}$ 18.7-19.3; its hardness is 6.5-7.5, melting point is 3410° C., boiling point is 5900° C., specific heat (20° C.) is 0.032 cal/g/° C., heat of fusion is 44 cal/g, heat of vaporization is 1150 cal/g and electrical resistivity (20° C.) is 5.5 μohm-cm. Tungsten is stable in dry air at ordinary temperatures, but forms the trioxide at red heat, is not attacked by water, but is oxidized to the dioxide by steam. Particulate tungsten can be pyrophoric under the right conditions and is slowly sol in fused potassium hydroxide or sodium carbonate in presence of air; is soluble in a fused mixture of NaOH and nitrate. Tungsten is attacked by fluorine at room temperature; by chlorine at 250-300° C. giving the hexachloride in absence of air, and the trioxide and oxychloride in the presence of air. In summary the melting point is 3410° C., the boiling point is 5900° C. and the density is $d_4^{20}$ 18.7-19.3.

Uranium (U) has an atomic weight of 238.0289 (characteristic naturally occurring isotopic mixture); an atomic number of 92 with no stable nuclides. Naturally occurring isotopes are 238 (99.275%); 235 (0.718%); 234 (0.005%); artificial radioactive isotopes are 226-233; 236; 237; 239; 240. Uranium comprises about 2.1 ppm of the earth's crust. Main uranium ores of commercial interest are carnotite, pitchblende, tobemite and autunite. Commercially important mines are located in Elliot Lake-Blind River area in Canada, Rand gold fields in South Africa, Colorado and Utah in the United States, in Australia and in France. The discovery from pitchblende is found in M. H. Klaproth, *Chem. Ann.* II, 387 (1789). Preparation of the metal is found in E. Peligot, *C. R. Acad. Sci* 12, 735 (1841) and Idem, *Ann. Chim. Phys.* 5, 5 (1842). Flowsheet and details of preparation of pure uranium metal are found in *Chem. Eng.* 62, No. 10, 113 (1955); Spedding et al., U.S. Pat. No. 2,852,364 (1958 to U.S.A.E.C.). *Reviews: Mellor's* Vol. XII, 1-138 (1932); C. D. Harrington, A. R. Ruehle, *Uranium Production Technology* (Van Nostrand, Princeton, 1959); E. H. P. Cordfunke, *The Chemistry of Uranium* (Elsevier, New York, 1969) 2550 pp; several authors in *Handb. Exp. Pharmakol,* 36, 3-306 (1973); "The Actinides," in *Comprehensive Inorganic Chemistry* Vol. 5, J. C. Bailar, Jr., et al., Eds. (Pergamon Press, Oxford, 1973) passim; F. Weigel in *Kirk-Othmer Encyclopedia of Chemical Technology* Vol. 23 (Wiley-Interscience, New York, 3rd ed., 1983) pp 502-547; idem in *The Chemistry of the Actinide Elements* Vol. 1, J. J. Katz et al., Eds. (Chapman and Hall, New York 1986) pp 169-442; J. C. Spirlet et al., *Adv. Inorg. Chem.* 31, 1-40 (1987). A review of toxicology and health effects is found in *Toxicological Profile for Uranium* (PB91-180471, 1990) 205 pp. Uranium is a silver-white, lustrous, radioactive metal that is both malleable and ductile, and tarnishes rapidly in air forming a layer of dark-colored oxide. Heat of vaporization is 446.7 kJ/mol; heat of fusion is 19.7 kJ/mol; heat of sublimation is 487.9 kJ/mol. Finely divided uranium metal and some uranium compounds may ignite spontaneously in air or oxygen and are rapidly soluble in aqueous HCl. Non-oxidizing acids such as sulfuric, phosphoric and hydrofluoric react only very slowly with uranium; nitric acid dissolves uranium at a moderate rate; and dissolution of finely divided Uranium in nitric acid may approach explosive violence. Uranium metal is inert to alkalis. In summary, the melting point is 1132.8±0.8° and density is 19.07; d 18.11; d 18.06.

Osmium (O) has an atomic weight of 190.23; an atomic number of 76 and is in Group VIII(8). Naturally occurring isotopes are 184 (0.02%); 186 (1.6%); 187 (1.6%); 188 (13.3%); 189 (16.1%); 190 (26.4%); 192 (41.0%). Artificial radioactive isotopes are 181-183; 185; 191; 193-195. Osmium comprises about 0.001 ppm of the earth's crust and is found in the mineral osmiridium and in all platinum ores. Tennant discovered osmium in 1804. Preparation is found in Berzelius et al., cited by Mellor, *A Comprehensive Treatise on Inorganic and Theoretical Chemistry* 15, 6887 (1936). *Reviews*: Gilchrist, *Chem. Rev.* 32, 277-372 (1943); Beamish et al., in *Rare Metals Handbook*, C. A. Hampel, Ed. (Reinhold New York, 1956) pp 291-328; Griffith, *Quart. Rev.* 19, 254-273 (1965); idem, *The Chemistry of the Rarer Platinum Metals* (John Wiley, New York, 1967) pp 1-125; Livingstone in *Comprehensive Inorganic Chemistry*, Vol. 3, J. C. Bailar, Jr. et al. Eds. (Pergamon Press, Oxford, 1973) pp 1163-1189, 1209-1233. Osmium is a bluish-white, lustrous metal with a close-packed hexagonal structure. With a density of $d_4^{20}$ 22.61, it has been long believed to be the densest element. X-ray data has shown it to be slightly less dense than iridium with a melting point of about 2700° C., boiling point of about 5500° C., a density of $d_4^{20}$ 22.61, specific heat (0° C.) 0.0309 cal/g/° C. and hardness 7.0 on Mohs' scale. Osmium is stable in cold air and, when finely divided, is slowly oxidized by air even at ordinary temperature to form tetroxide. Osmium is attacked by fluorine above 100° C., by dry chlorine on heating, but not attacked by bromine or iodine. Osmium is attacked by aqua regia, by oxidizing acids over a long period of time, but barely affected by HCl, $H_2SO_4$. Osmium burns in vapor of phosphorus to form a phosphide, in vapor of sulfur to form a sulfide. Osmium is also attacked by molten alkali hydrosulfates, by potassium hydroxide and oxidizing agents. Finely divided osmium absorbs a considerable amount of hydrogen. In summary, osmium has a melting point of about 2700° C., a boiling point of about 5500° C. and a density of $d_4^{20}$ 22.61.

Iridium (Ir) has an atomic weight of 192.217 and an atomic number of 77. Naturally occurring isotopes are 191 (38.5%); 193 (61.5%) and artificial radioactive isotopes are 182-191; 194-198. It comprises about 0.001 ppm of the earth's crust. Iridium was discovered by Tennant. It occurs in nature in the metallic state, usually as a natural alloy with osmium (osmiridium) and found in small quantities alloyed with native platinum (platinum mineral) or with native gold. Recovery and purification from osmiridium are found in Deville, Debray, *Ann. Chim. Phys.* 61, 84 (1861); from the platinum mineral: Wichers, *J. Res. Nat. Bur. Stand.* 10, 819 (1933). *Reviews* of preparation, properties and chemistry of iridium and other platinum metals: Gilchrist, *Chem. Rev.* 32, 277-372 (1943); W. P. Griffith, *the Chemistry of the Rare Platinum Metals*

(John Wiley, New York, 1967) pp 1-41, 227-312; Livingstone in *Comprehensive Inorganic Chemistry* Vol. 3, J. C. Bailar Jr. et al., Eds. (Pergamon Press, Oxford, 1973) pp 1163-1189, 1254-1274. Iridium is a silver-white, very hard metal; face-centered cubic lattice with a melting point of 2450° C., boiling point of about 4500° C. with a density of $d_4^{20}$ 22.65, specific heat of 0.0307 cal/g/° C., Mohs' hardness of 6.5 and has the highest specific gravity of all elements. Pure iridium is not attacked by any acids including aqua regia and only slightly by fused (non-oxidizing) alkalis. It is superficially oxidized on heating in the air, is attacked by fluorine and chlorine at a red heat, attacked by potassium sulfate or by a mixture of potassium hydroxide and nitrate on fusion, attacked by lead, zinc or tin. The powdered metal is oxidized by air or oxygen at a red heat to the dioxide, $IrO_2$, but on further heating the dioxide dissociates into its constituents. In summary, iridium has a melting point of 2450° C., a boiling point of about 4500° C. and a density of $d_4^{20}$ 22.65.

Platinum (Pt) has an atomic weight of 195.078, an atomic number of 78 and is in Group VIII(10). Naturally occurring isotopes are 190 (0.01%); 192 (0.8%); 194 (32.9%; 195 (33.8%); 196 (25.2%); 198 (7.2%); 190 is radioactive: $T_{1/2}$ $6.9 \times 10^{11}$ years. Artificial radioactive isotopes are 173-189; 191; 193; 197; 199-201. Platinum comprises about 0.01 ppm of the earth's crust. It is believe to be mentioned by Pliny under the name "alutiae" and has been known and used in South America as "platina del Pinto". Platinum was reported by Ulloa in 1735; brought to Europe by Wood, and described by Watson in 1741. It occurs in native form alloyed with one or more members of its group (iridium, osmium, palladium, rhodium, and ruthenium) in gravels and sands. Preparation is found in Wichers et al, *Trans. Amer. Inst. Min. Met. Eng.* 76, 602 (1928). *Reviews* of preparation, properties and chemistry of platinum and other platinum metals: Gilchrist, *Chem. Rev.* 32, 277-372 (1943); Beamish et al., *Rare Metals Handbook*, C. A. Hampel, Ed. (Reinhold, New York, 1956) pp 291-328; Livingstone, *Comprehensive Inorganic chemistry*, Vol. 3, J. C. Bailar, Jr. et al., Eds. (Pergamon press, Oxford, 1973) pp 1163-1189, 1330-1370; F. R. Harley, *The Chemistry of Platinum and Palladium with Particular Reference to Complexes of the Elements* (Halsted Press, New York, 1973). Platinum is a silver-gray, lustrous, malleable and ductile metal; face-centered cubic structure; prepared in the form of a black powder (platinum black) and as spongy masses (platinum sponge). Platinum has a melting point of 1773.5±1° C.; Roeser et al., *Nat Bur. Stand. J. Res.* 6, 1119 (1931); boiling point of about 3827° C. with a density of $d_4^{20}$ 21.447 (calcd.); Brinell hardness of 55; specific heat of 0.0314 cal/g at 0° C.; electrical resistivity (20° C.) of 10.6 µohm-cm.; does not tarnish on exposure to air, absorbs hydrogen at a red heat and retains it tenaciously at ordinary temperature; gives off the gas at a red heat in vacuo; occludes carbon monoxide, carbon dioxide, nitrogen; volatilizes considerably when heated in air at 1500° C. The heated metal absorbs oxygen and gives it off on cooling. Platinum is not affected by water or by single mineral acids, reacts with boiling aqua regia with formation of chloroplatinic acid, and also with molten alkali cycanides. It is attacked by halogens, by fusion with caustic alkalis, alkali metrates, alkali peroxides, by arsenates and phosphates in the presence of reducing agents. In summary, platinum has a melting point of 1773.5±1° C.; Roeser et al., *Nat. Bur. Stand. J. Res.* 6, 1119 (1931), boiling point about 3827° C. and a density of 21.447 (calcd).

Gold (Au) has an atomic weight of 196.96655; an atomic number of 79 and is in Group IB(11). Naturally occurring isotope 197; artificial isotopes (mass numbers) are 177-179, 181, 183, 185-196, 198-203. Gold comprises 0.005 of the earth's crust. Gold is probably the first pure metal known to man. It occurs in nature in its native form and in minute quantities in almost all rocks and in seawater. Gold ores including calavarite ($AuTe_2$), sylvanite [$(Ag,Au)Te_2$], petzite [$(Ag,Au)_2Te$]. Methods of mining, extracting and refining are found in Hull, Stent, in *Modern Chemical Processes*, Vol. 5 (Reinhold, New York, 1958) pp 60-71. Laboratory preparation of gold powder from gold pieces is found in Block, *Inorg. Syn* 4, 15 (1953). Chemistry of gold drugs in the treatment of rheumatoid arthritis is found in D. H. Brown, W. E. Smith, *Chem. Soc. Rev.* 9, 217 (1980). Use as a catalyst in oxidation of organic compounds by $NO_2$ is found in R. E. Sievers, S. A. Nyarady, *J. Am. Chem. Soc.* 107, 3726 (1985). Least reactive metal at interfaces with gas or liquid is found in B. Hammer, J. K. Norskov, *Nature* 373, 238 (1995). Reviews: *Gmelin's Handb. Anorg. Chem., Gold* (8th ed.) 62, parts 2, 3 (1954); Johnson, Davis, "Gold" in *Comprehensive Inorganic Chemistry*, Vol. 3, J. C. Bailar Jr. et al., Eds. (Pergamon Press, Oxford, 1973) pp 129-186; J. G. Cohn, E. W. Stem in *Kirk-Othmer Encyclopedia of Chemical Technology* Vol. 11 (Wiley Interscience, New York, 3rd ed., 1980) pp 972-995. Gold is a yellow, soft metal; face-centered cubic structure; and when prepared by volatilization or precipitation methods, deep violet, purple, or ruby powder, melting point of 1064.76° C.; boiling point of 2700° C. with a density of 19.3; Moh's hardness of 2.5-3.0; Brinell hardness of 18.5. Gold is extremely inactive; not attacked by acids, air or oxygen; superficially attacked by aq halogens at room temperature; reacts with aqua regia, with mixtures containing chlorides, bromides or iodides if they can generate nascent halogens, with many oxidizing mixtures especially those containing halogens, alkali cyanides, solutions of thiocyanates and double cyanides. In summary, gold has a melting point of 1064.76° C., boiling point of 2700° C. and density of 19.3.

Rhenium (Re) has an atomic weight of 186.207; an atomic number of 75 and is in Group VIIB(7). Naturally occurring isotopes are 185 (37.07%); 187 (62.93%), the latter is radioactive, $T_{1/2} \sim 10^{11}$ years; artificial radioactive isotopes are 177-184; 186; 188-192. Rhenium comprises about 0.001 ppm of the earth's crust. It occurs in gadolinite, molybdenite, columbite, rare earth minerals, and some sulfide ores. Rhenium was discovered by Nodack et al, *Naturwiss.* 13, 567, 571 (1925). Preparation of metallic rhenium by reduction of potassium perrhenate or ammonium perrhenate is found in Hurd, Brim, *Inorg. Syn* 1, 175 (1939) and preparation of high purity rhenium is found in Rosenbaum et al., *J. Electrochem. Soc.* 103, 18 (1956). *Reviews*: Mealaven in rare *Metals Handbook*, C. A. Hampel, Ed. (Reinhold, New York, 1954) pp 347-364; Peacock in *Comprehensive Inorganic Chemistry* Vol. 3, J. C. Bailar, Jr. et al., Eds. (Pergamon Press, Oxford, 1973) pp 905-978; P. M. Treichel in *Kirk-Othmer Encyclopedia of Chemical Technology* Vol. 20 (Wiley-Interscience, New York, 3rd ed., 1982) pp 249-258. Rhenium has hexagonal close-packed crystals, black to silver-gray; has a density of d 21.02; melting point of 3180° C.; boiling point of 5900° C. (estimated); specific heat of 0-20° C. 0.03263 cal/g/° C.; specific electrical resistance of $0.21 \times 10^{-4}$ ohm/cm at 20° C.; Brinell hardness of 250; latent heat of vaporization of 152 kcal/mol and reacts with oxidizing acids, nitric and concentrated sulfuric acid, but not with HCl. In summary, Rhenium has a melting point of 3180° C., boiling point of 5900° C. (estimated) and density of 21.02.

Neptunium (Np) has an atomic number of 93. It is the first man-made transuranium element with no stable nuclides. Known isotopes (mass numbers) are 227-242. The discovery of isotope 239 ($T_{1/2}$ 2.355 days, alpha-decay, relative atomic mass of 239.0529) can be found in E. McMillan, P. Abelson, Phys. Rev. 57, 1185 (1940); of isotope 237 ($T_{1/2}$ 2.14×10⁶ years, the longest-lived known isotope, relative atomic mass of 237.0482) can be found at A. C. Wahl, G. T. Seaborg, ibid. 73, 940 (1948). Preparation of metal is found in S. Fried, N. Davidson, *J. Am. Chem. Soc.* 70, 3539 (1948); L. B. Magnusson, T J. LaChapelle, ibid. 3534. Neptunium's presence in nature is found in Seaborg, Perlman, ibid. 70, 1571 (1948). Chemical properties are found in Seaborg, Wahl, ibid. 1128. Reviews: C. Keller, *the chemistry of the Transactinide Elements* (Verlag Chemie, Weinheim, English Ed., 1971) pp 253-332; W. W. Schulz, G. E. Benedict, *Neptunium-237; Production and Recovery*, AEC Critical Review Series (US-AEC, Washington D.C.), 1972) 85 pp; *Comprehensive Inorganic Chemistry* Vol. 5, J. C. Bailar, Jr. et al., Eds. (Pergamon Press, Oxford, 1973) passim; J. A. Fahey in *The Chemistry of the Actinide Elements* Vol. 1, J. J. Katz et al., Eds (Chapman and Hall, New York, 1986) pp 443-498; G. T. Seaborg in *Kirk-Othmer Encyclopedia of Chemical Technology* Vol. 1 (Wiley-Interscience, New York, 4th ed., 1991) pp 412-444. Neptunium is a silvery metal; develops a thin oxide layer upon exposure to air for short periods. It reacts with air at high temperatures to form $NpO_2$ with an extrapolated boiling point of 4174° C. Neptunium has been obtained in its five oxidation states in solution; the most stable is the pentavalent state. Tetravalent Neptunium is readily oxidized to the hexavalent state by permanganate in the cold, or by strong oxidizing agents; on electrolytic reduction in an atmosphere of nitrogen, the trivalent form is obtained. In summary, Neptunium has a melting point of 637° C.; a boiling point of 4174° C. and a density of d 20.45; d 19.36.

Plutonium (Pu) has an atomic number of 94 with no stable nuclides. Known isotopes (mass numbers) are 232-246. the longest-lived known isotopes are $^{242}$Pu ($T_{1/2}$ 3.76×10⁵ years, relative atomic mass 242.0587), 244 ($T_{1/2}$ 8.26×10⁷ years, relative atomic mass 244.0642). Commercially useful isotopes are $^{238}$Pu ($T_{1/2}$ 87.74 years, relative atomic mass 238.0496); $^{239}$Pu ($T_{1/2}$ 2.41×10⁴ years; relative atomic mass 239.0522). Plutonium comprises $10^{-22}$% of the earth's crust. The discovery of isotope $^{238}$Pu is found in G. T. Seaborg et al., *Phys. Rev.* 69, 366, 367 (1946); of isotope $^{239}$Pu in J. W. Kennedy et al., ibid 70 555 (1946). Solution of $^{239}$Pu from pitchblende is found in G. T. Saborg, M. L. Perlman, *J. Am. Chem. Soc.* 70, 1571 (1948). Preparation of metal is found in B. B. Cunningham, L. B. Werner, ibid. 71, 1521 (1949). Chemical properties are found in Seaborg, Wal, ibid. 1128; Harvey et al., *J. Chem. Soc.* 1947, 1010. Reviews: J. M. Cleveland, *the Chemistry of Plutonium* (Gordon & Breach, New York, 1970) 653 pp; C. Keller, *The Chemistry of the Transuranium Elements* (Verlag Chemie, Weinheim, English Ed., 1971) pp 333-484; *Comprehensive Inorganic Chemistry* Vol. 5, J. C. Bailar, Jr. et al., Eds. (Pergamon Press, Oxford, 1973) passim; *Handb. Exp. Pharmakol* 36 307-688 (1973); F. Weigel in *Kirk-Othmer Encyclopedia of Chemical Technology* Vol. 18 (Wiley-Interscience, New York, 3rd ed., 1982) pp 278-301; *Plutonium Chemistry*, W. T. Carnall, G. R. Choppin, Eds. (Am. Chem. Soc., Washington, D.C., 1983) 484 pp; F. Weigel et al in *The Chemistry of the Actinide Elements* Vol. 1, J. J. Katz et al., Eds. (Chapman and Hall, New York, 1986) pp 499-886. Review of toxicology is found in W. J. Bair, R. C. Thompson, *Science* 183, 715-722 (1974); and health effects are found in *Toxicological Profile for Plutonium* (PB91-180406, 1990) 206 pp. Plutonium is a silvery-white metal that is highly reactive. It oxidizes readily in dry air and oxygen, the rate increasing in the presence of moisture. In summary, Plutonium has a melting point of 640±2° C. and densities of $d^{21}$ 19.86; $d^{190}$ 17.70; $d^{235}$ 17.14; $d^{320}$ 15.92; $d^{450}$ 16.00; $d^{490}$ 16.51.

Tantalum (Ta) has an atomic weight of 180.9479; atomic number of 73 and is in Group VB(5). Naturally occurring isotopes are 181 (99.9877%); 180 (0.0123%), $T_{1/2}$>10¹² years; artificial radioactive isotopes are 172-179; 182-186. Tantalum occurs almost invariably with niobium, but less abundant than niobium. It is found in the minerals columbite, q.v., tantalite ([(Fe,Mn)(Ta,Nb)$_2$O$_6$] and microlite [(Na,Ca)$_2$Ta$_2$O$_6$(O,OH,F)]. Tantalum was discovered by Edeberg in 1802; first obtained pure by Bolton in *Z. Elektrochem.* 11, 45 (1905). Preparation is found in Schoeller, Powell, *J. Chem. Soc.* 119, 1927 (1921). Reviews: G. L. Miller, *Tantalum and Niobium* (Academic Press, New York, 1959) 767 pp; Brown, "The Chemistry of Niobium and Tantalum" in *Comprehensive Inorganic Chemistry* Vol. 3, J. C. Bailar, Jr. et al., Eds. (Pergamon Press, Oxford, 1973) pp 553-622. Tantalum is a gray, very hard, malleable, ductile metal that can be readily drawn in fine wires; has a melting point of 2996° C.; a boiling point of 5429° C., a density of d 16.69; specific heat 0° C.: 0.036 cal/g/° C.; electrical resistivity (18° C.): 12.4 μohm-cm; insoluble in water; very resistant to chemical attack; not attacked by acids other than hydrofluoric and not attacked by aqueous alkalis; slowly attacked by fused alkalis. It reacts with fluorine, chlorine and oxygen only on heating and at high temperatures absorbs several hundred times its volume of hydrogen; combines with nitrogen, with carbon. In summary, Tantalum has a melting point of 2996° C., boiling point of 5429° C. and a density of d 16.69.

A large variety of polymer materials can be used in the composite materials of the invention. For the purpose of this disclosure, a polymer is a general term covering either a thermoset or a thermoplastic. We have found that polymer materials useful in the invention include both condensation polymeric materials and vinyl polymeric materials. Included are both vinyl and condensation polymer blends, and polymeric alloys thereof. Vinyl polymers are typically manufactured by the polymerization of monomers having an ethylenically unsaturated olefinic group. Condensation polymers are typically prepared by a condensation polymerization reaction which is typically considered to be a stepwise chemical reaction in which two or more molecules combined, often but not necessarily accompanied by the separation of water or some other simple, typically volatile substance. Such polymers can be formed in a process called polycondensation. The polymer has a density of at least 0.85 gm-cm⁻³, however, polymers having a density of 0.96 to 2 gm-cm⁻³ and preferably greater than 0.98 to 1.9 gm-cm⁻³ are useful to increase density. Preferred polymers can have a useful high density typically greater than 1 gm-cm⁻³ often greater than 1.5 gm-cm⁻³ and also greater than 1.7 gm-cm⁻³ depending on metal and end use.

Vinyl polymers include polyethylene, polypropylene, polybutylene, acrylonitrile-butadiene-styrene (ABS), polybutylene copolymers, polyacetyl polymers, polyacrylic polymers, homopolymers or copolymers comprising vinyl chloride, vinylidene chloride, fluorocarbon copolymers, etc. Condensation polymers include nylon, phenoxy polymers, polyarylether such as polyphenylether, polyphenylsulfide materials; polycarbonate materials, chlorinated polyether polymers, polyethersulfone polymers, polyphenylene oxide polymers, polysulfone polymers, polyimide polymers, thermoplastic urethane elastomers, polyester (i.e. polyethylene terephthalate) and many other polymer materials.

Condensation polymers that can be used in the composite materials of the invention include polyamides, polyamide-imide polymers, polyarylsulfones, polycarbonate, polybutylene terephthalate, polybutylene naphthalate, polyetherimides, polyethersulfones, polyethylene terephthalate, thermoplastic polyimides, polyphenylene ether blends, polyphenylene sulfide, polysulfones, thermoplastic polyurethanes and others. Preferred condensation engineering polymers include polycarbonate materials, polyphenyleneoxide materials, and polyester materials including polyethylene terephthalate, polybutylene terephthalate, polyethylene naphthalate and polybutylene naphthalate materials.

Polycarbonate engineering polymers are high performance, amorphous engineering thermoplastics having high impact strength, clarity, heat resistance and dimensional stability. Polycarbonates are generally classified as a polyester or carbonic acid with organic hydroxy compounds. The most common polycarbonates are based on phenol A as a hydroxy compound copolymerized with carbonic acid. Materials are often made by the reaction of a bisphenol A with phosgene ($O=CCl_2$). Polycarbonates can be made with phthalate monomers introduced into the polymerization extruder to improve properties such as heat resistance, further trifunctional materials can also be used to increase melt strength or extrusion blow molded materials. Polycarbonates can often be used as a versatile blending material as a component with other commercial polymers in the manufacture of alloys. Polycarbonates can be combined with polyethylene terephthalate acrylonitrile-butadiene-styrene polymers, styrene maleic anhydride polymers and others. Preferred alloys comprise a styrene copolymer and a polycarbonate. Preferred melt for the polycarbonate materials should be indices between 0.5 and 30, preferably between 1 and 20 gms/10 min.

A variety of polyester condensation polymer materials including polyethylene terephthalate, polybutylene terephthalate, polyethylene naphthalate, polybutylene naphthalate, etc. can be useful in the composites of the invention. Polyethylene terephthalate and polybutylene terephthalate are high performance condensation polymer materials. Such polymers often made by a copolymerization between a diol (ethylene glycol, 1,4-butane diol) with dimethyl terephthalate. In the polymerization of the material, the polymerization mixture is heated to high temperature resulting in the transesterification reaction releasing methanol and resulting in the formation of the engineering plastic. Similarly, polyethylene naphthalate and polybutylene naphthalate materials can be made by copolymerizing as above using as an acid source, a naphthalene dicarboxylic acid. The naphthalate thermoplastics have a higher Tg and higher stability at high temperature compared to the terephthalate materials. However, all these polyester materials are useful in the composite materials of the invention. Such materials have a preferred molecular weight characterized by melt flow properties. Useful polyester materials have a viscosity at 265° C. of about 500-2000 cP, preferably about 800-1300 cP.

Polyphenylene oxide materials are engineering thermoplastics that are useful at temperature ranges as high as 330° C. Polyphenylene oxide has excellent mechanical properties, dimensional stability, and dielectric characteristics. Commonly, phenylene oxides are manufactured and sold as polymer alloys or blends when combined with other polymers or fiber. Polyphenylene oxide typically comprises a homopolymer of 2,6-dimethyl-1-phenol. The polymer commonly known as poly(oxy-(2,6-dimethyl-1,4-phenylene)). Polyphenylene is often used as an alloy or blend with a polyamide, typically nylon 6-6, alloys with polystyrene or high impact styrene and others. A preferred melt index (ASTM 1238) for the polyphenylene oxide material useful in the invention typically ranges from about 1 to 20, preferably about 5 to 10 gm/10 min. The melt viscosity is about 1000 at 265° C.

Another class of thermoplastic includes styrenic copolymers. The term styrenic copolymer indicates that styrene is copolymerized with a second vinyl monomer resulting in a vinyl polymer. Such materials contain at least a 5 mol-% styrene and the balance being 1 or more other vinyl monomers. An important class of these materials is styrene acrylonitrile (SAN) polymers. SAN polymers are random amorphous linear copolymers produced by copolymerizing styrene acrylonitrile and optionally other monomers. Emulsion, suspension and continuous mass polymerization techniques have been used. SAN copolymers possess transparency, excellent thermal properties, good chemical resistance and hardness. These polymers are also characterized by their rigidity, dimensional stability and load bearing capability. Olefin modified SAN's (OSA polymer materials) and acrylic styrene acrylonitriles (ASA polymer materials) are known. These materials are somewhat softer than unmodified SAN's and are ductile, opaque, two phased terpolymers that have surprisingly improved weatherability.

ASA polymers are random amorphous terpolymers produced either by mass copolymerization or by graft copolymerization. In mass copolymerization, an acrylic monomer styrene and acrylonitrile are combined to form a heteric terpolymer. In an alternative preparation technique, styrene acrylonitrile oligomers and monomers can be grafted to an acrylic elastomer backbone. Such materials are characterized as outdoor weatherable and UV resistant products that provide excellent accommodation of color stability property retention and property stability with exterior exposure. These materials can also be blended or alloyed with a variety of other polymers including polyvinyl chloride, polycarbonate, polymethyl methacrylate and others. An important class of styrene copolymers includes the acrylonitrile-butadiene-styrene monomers. These polymers are very versatile family of engineering thermoplastics produced by copolymerizing the three monomers. Each monomer provides an important property to the final terpolymer material. The final material has excellent heat resistance, chemical resistance and surface hardness combined with processability, rigidity and strength. The polymers are also tough and impact resistant. The styrene copolymer family of polymers have a melt index that ranges from about 0.5 to 25, preferably about 0.5 to 20.

An important class of engineering polymers that can be used in the composites of the invention include acrylic polymers. Acrylics comprise a broad array of polymers and copolymers in which the major monomeric constituents are an ester acrylate or methacrylate. These polymers are often provided in the form of hard, clear sheet or pellets. Acrylic monomers polymerized by free radical processes initiated by typically peroxides, azo compounds or radiant energy. Commercial polymer formulations are often provided in which a variety of additives are modifiers used during the polymerization provide a specific set of properties for certain applications. Pellets made for polymer grade applications are typically made either in bulk (continuous solution polymerization), followed by extrusion and pelleting or continuously by polymerization in an extruder in which unconverted monomer is removed under reduced pressure and recovered for recycling. Acrylic plastics are commonly made by using methyl acrylate, methylmethacrylate, higher alkyl acrylates and other copolymerizable vinyl monomers. Preferred acrylic polymer materials useful in the composites of the invention has a melt index of about 0.5 to 50, preferably about 1 to 30 gm/10 min.

Vinyl polymers include a acrylonitrile; polymer of alpha-olefins such as ethylene, propylene, etc.; chlorinated monomers such as vinyl chloride, vinylidene dichloride, acrylate monomers such as acrylic acid, methylacrylate, methylmethacrylate, acrylamide, hydroxyethyl acrylate, and others;

styrenic monomers such as styrene, alphamethyl styrene, vinyl toluene, etc.; vinyl acetate; and other commonly available ethylenically unsaturated monomer compositions.

Polymer blends or polymer alloys can be useful in manufacturing the pellet or linear extrudate of the invention. Such alloys typically comprise two miscible polymers blended to form a uniform composition. Scientific and commercial progress in the area of polymer blends has lead to the realization that important physical property improvements can be made not by developing new polymer material but by forming miscible polymer blends or alloys. A polymer alloy at equilibrium comprises a mixture of two amorphous polymers existing as a single phase of intimately mixed segments of the two macro molecular components. Miscible amorphous polymers form glasses upon sufficient cooling and a homogeneous or miscible polymer blend may exhibit a single, composition dependent glass transition temperature (Tg). Immiscible or non-alloyed blend of polymers typically displays two or more glass transition temperatures associated with immiscible polymer phases. In the simplest cases, the properties of polymer alloys reflect a composition weighted average of properties possessed by the components. In general, however, the property dependence on composition varies in a complex way with a particular property, the nature of the components (glassy, rubbery or semi-crystalline), the thermodynamic state of the blend, and its mechanical state whether molecules and phases are oriented.

The primary requirement for the substantially thermoplastic engineering polymer material is that it retain sufficient thermoplastic properties such as viscosity and stability, to permit melt blending with a metal particulate, permit formation of linear extrudate pellets, and to permit the composition material or pellet to be extruded or injection molded in a thermoplastic process forming the useful product. Engineering polymer and polymer alloys are available from a number of manufacturers including B.F. Goodrich, G.E., Dow, Dyneon LLC and duPont.

Polyester polymers are manufactured by the reaction of a dibasic acid with a glycol. Dibasic acids used in polyester production include phthalic anhydride, isophthalic acid, maleic acid and adipic acid. The phthalic acid provides stiffness, hardness and temperature resistance; maleic acid provides vinyl saturation to accommodate free radical cure; and adipic acid provides flexibility and ductility to the cured polymer. Commonly used glycols are propylene glycol which reduces crystalline tendencies and improves solubility in styrene. Ethylene glycol and diethylene glycol reduce crystallization tendencies. The diacids and glycols are condensed eliminating water and are then dissolved in a vinyl monomer to a suitable viscosity. Vinyl monomers include styrene, vinyltoluene, paramethylstyrene, methylmethacrylate, and diallyl phthalate. The addition of a polymerization initiator, such as hydroquinone, tertiary butylcatechol or phenothiazine extends the shelf life of the uncured polyester polymer. Polymers based on phthalic anhydride are termed orthophthalic polyesters and polymers based on isophthalic acid are termed isophthalic polyesters. The viscosity of the unsaturated polyester polymer can be tailored to an application. Low viscosity is important in the fabrication of fiber-reinforced composites to ensure good wetting and subsequent high adhesion of the reinforcing layer to the underlying substrate. Poor wetting can result in large losses of mechanical properties. Typically, polyesters are manufactured with a styrene concentration or other monomer concentration producing polymer having an uncured viscosity of 200-1,000 mPa.s(cP). Specialty polymers may have a viscosity that ranges from about 20 cP to 2,000 cP. Unsaturated polyester polymers are typically cured by free radical initiators commonly produced using peroxide materials. Wide varieties of peroxide initiators are available and are commonly used. The peroxide initiators thermally decompose forming free radical initiating species.

Phenolic polymers can also be used in the manufacture of the structural members of the invention. Phenolic polymers typically comprise a phenol-formaldehyde polymer. Such polymers are inherently fire resistant, heat resistant and are low in cost. Phenolic polymers are typically formulated by blending phenol and less than a stoichiometric amount of formaldehyde. These materials are condensed with an acid catalyst resulting in a thermoplastic intermediate polymer called NOVOLAK. These polymers are oligomeric species terminated by phenolic groups. In the presence of a curing agent and optional heat, the oligomeric species cure to form a very high molecular weight thermoset polymer. Curing agents for novalaks are typically aldehyde compounds or methylene ($—CH_2—$) donors. Aldehydic curing agents include paraformaldehyde, hexamethylenetetraamine, formaldehyde, propionaldehyde, glyoxal and hexamethylmethoxy melamine.

The fluoropolymers useful in this invention are polymers made with monomers containing one or more atoms of fluorine, or copolymers of two or more of such monomers. Common examples of fluorinated monomers useful in these polymers or copolymers include tetrafluoroethylene (TFE), hexafluoropropylene(HFP), vinylidene fluoride (VDF), perfluoroalkylvinyl ethers such as perfluoro-(n-propyl-vinyl) ether (PPVE) or perfluoromethylvinylether (PMVE). Other copolymerizable olefinic monomers, including non-fluorinated monomers, may also be present.

Particularly useful materials for the fluoropolymers are TFE-HFP-VDF terpolymers (melting temperature of about 100 to 260° C.; melt flow index at 265° C. under a 5 kg load is about 1-30 g-10 $min^{-1}$.), hexafluoropropylene-tetrafluoroethylene-ethylene (HTE) terpolymers (melting temperature about 150 to 280° C.; melt flow index at 297° C. under a 5 kg load of about 1-30 g-10 $min^{-1}$.), ethylene-tetrafluoroethylene (ETFE) copolymers (melting temperature about 250 to 275° C.; melt flow index at 297° C. under a 5 kg load of about 1-30 g-10 $min^{-1}$.), hexafluoropropylene-tetrafluoroethylene (FEP) copolymers (melting temperature about 250 to 275° C.; melt flow index at 372° C. under a 5 kg load of about 1-30 g-10 $min^{-1}$.), and tetrafluoroethylene-perfluoro(alkoxy alkane) (PFA) copolymers (melting temperature about 300 to 320° C.; melt flow index at 372° C. under a 5 kg load of about 1-30 g-10 $min^{-1}$.). Each of these fluoropolymers is commercially available from Dyneon LLC, Oakdale, Minn. The TFE-HFP-VDF terpolymers are sold under the designation "THV".

Also useful are vinylidene fluoride polymers primarily made up of monomers of vinylidene fluoride, including both homopolymers and copolymers. Such copolymers include those containing at least 50 mole percent of vinylidene fluoride copolymerized with at least one comonomer selected from the group consisting of tetrafluoroethylene, trifluoroethylene, chlorotrifluoroethylene, hexafluoropropene, vinyl fluoride, pentafluoropropene, and any other monomer that readily copolymerizes with vinylidene fluoride. These materials are further described in U.S. Pat. No. 4,569,978 (Barber)

incorporated herein by reference. Preferred copolymers are those composed of from at least about 70 and up to 99 mole percent vinylidene fluoride, and correspondingly from about 1 to 30 percent tetrafluoroethylene, such as disclosed in British Patent No. 827,308; and about 70 to 99 percent vinylidene fluoride and 1 to 30 percent hexafluoropropene (see for example, U.S. Pat. No. 3,178,399); and about 70 to 99 mole percent vinylidene fluoride and 1 to 30 percent trifluoroethylene. Terpolymers of vinylidene fluoride, trifluoroethylene and tetrafluoroethylene such as described in U.S. Pat. No. 2,968,649 and terpolymers of vinylidene fluoride, trifluoroethylene and tetrafluoroethylene are also representative of the class of vinylidene fluoride copolymers which are useful in this invention. Such materials are commercially available under the KYNAR trademark from Arkema Group located in King of Prussia, Pa. or under the DYNEON trademark from Dyneon LLC of Oakdale, Minn. Fluorocarbon elastomer materials can also be used in the composite materials of the invention. Fluoropolymer contain VF2 and HFP monomers and optionally TFE and have a density greater than 1.8 gm-cm$^{-3}$ and exhibit good resistance to most oils, chemicals, solvents, and halogenated hydrocarbons, and an excellent resistance to ozone, oxygen, and weathering. Their useful application temperature range is −40° C. to 300° C. Fluoroelastomer examples include those described in detail in Lentz, U.S. Pat. No. 4,257,699, as well as those described in Eddy et al., U.S. Pat. No. 5,017,432 and Ferguson et al., U.S. Pat. No. 5,061,965. The disclosures of each of these patents are totally incorporated herein by reference.

Latex fluoropolymers are available in the form of the polymers comprising the PFA, FEP, ETFE, The, THV and PVDF monomers. This class of latex system can act as an interfacial modifier and in a polymerized state with certain latex polymer systems.

Fluorinated poly(meth)acrylates can generally be prepared by free radical polymerization either neat or in solvent, using radical initiators well known to those skilled in the art. Other monomers which can be copolymerized with these fluorinated (meth)acrylate monomers include alkyl (meth)acrylates, substituted alkyl (meth)acrylates, (meth)acrylic acid, (meth)acrylamides, styrenes, vinyl halides, and vinyl esters. The fluoropolymers can comprise polar constituents. Such polar groups or polar group containing monomers may be anionic, nonionic, cationic, or amphoteric. In general, the more commonly employed polar groups or polar group-containing organic radicals include organic acids, particularly carboxylic acid, sulfonic acid and phosphonic acid; carboxylate salts, sulfonates, phosphonates, phosphate esters, ammonium salts, amines, amides, alkyl amides, alkyl aryl amides, imides, sulfonamides, hydroxymethyl, thiols, esters, silanes, and polyoxyalkylenes, as well as other organic radicals such as alkylene or arylene substituted with one or more of such polar groups. The latex fluoropolymers described herein are typically aqueous dispersed solids but solvent materials can be used. The fluoropolymer can be combined with various solvents to form emulsion, solution or dispersion in a liquid form. Dispersions of fluoropolymers can be prepared using conventional emulsion polymerization techniques, such as described in U.S. Pat. Nos. 4,418,186; 5,214,106; 5,639,838; 5,696,216 or *Modern Fluoropolymers*, Edited by John Scheirs, 1997 (particularly pp. 71-101 and 597-614) as well as assignees' copending patent application Ser. No. 01/03,195, filed Jan. 31, 2001.

The liquid forms can be further diluted in order to deliver the desired concentration. Although aqueous emulsions, solutions, and dispersions are preferred, up to about 50% of a cosolvent such as methanol, isopropanol, or methyl perfluorobutyl ether may be added. Preferably, the aqueous emulsions, solutions, and dispersions comprise less than about 30% cosolvent, more preferably less than about 10% cosolvent, and most preferably the aqueous emulsions, solutions, and dispersions are substantially free of cosolvent.

The metal particulate can be coupled to the polymer phase depending on the nature of the polymer phase, the filler, the particulate surface chemistry and any pigment process aid or additive present in the composite material. In general the mechanism used to couple metal particulate to polymer include interfacial modification, solvation, chelation, coordination bonding (ligand formation), etc.

Interfacial modifiers used in the composite fall into broad categories including, for example, stearic acid and derivatives, silane compounds, titanate compounds, zirconate compounds, aluminate compounds. The choice of interfacial modifiers is dictated by metal particulate, polymer, and application. The maximum density of a composite is a function of the densities of the materials and the volume fractions of each. Higher density composites are achieved by maximizing the per unit volume of the materials with the highest densities. Interfacial modifying chemistries are capable of modifying the surface of the particulate by coordination bonding, Van der Waals forces, covalent bonding, or a combination of all three. The surface of the particle behaves as a particle of the non-reacted end of the interfacial modifier. These organics reduce the friction between particles preventing gouging and allowing for greater freedom of movement between particles. These phenomena allow the applied shaping force to reach deeper into the form resulting in a more uniform pressure gradient. This achieves closer packing (note highest Van der Waals occurs at 5 Angstrom or less) in the bulk and higher physical properties. The use of a sufficient amount of the interfacial modifier that is sufficient to modify the surface characteristic of the metal but not displace polymer is an important compounding characteristic.

Stearic acid and derivatives or compounds thereof, modify the composites of the invention, stearic acid performs a interfacial modifying function to result in the formation of a stearic layer on the surface of the metal particle reducing the intermolecular forces, improving the tendency of the polymer to wet the particulate particle, and resulting in increased composite density.

Similarly, silane interfacial modifiers improve physical properties of the composites by forming chemical bonds between the metal particle and the continuous polymer phase, or by modifying the surface energy of the inorganic metal particulate matching the surface energy of the polymer at the particle polymer interface. Silane coupling agents useful in the invention include but are not limited to compounds of the following structure:

$$R\text{—}(CH_2)_n\text{—}Si\text{—}X_3$$

wherein X represents a hydrolyzable group comprising alkoxy-, acyloxy-, halo- or amino- depending on the surface chemistry of the metal particulate and the reaction mechanism. Coupling is maximized as the number of chemical bonds between the particulate surface and polymer is maximized. When a composite will be used in an application including large amounts of aqueous media and broad temperature excursions, dipodal silanes such as bis(triethoxysilyl) ethane are chosen. These materials have the following structure:

$$R[(CH_2)_n-Si-X_3]_2$$

wherein R represents the non-hydrolyzable organic group of the silane compound. The R group may be chemically bonded to the polymer phase or as desired to remain unreactive if non-bonded interfacial modifier can be applied. When R is chemically bonded to the polymer phase, the reaction proceeds through the addition of free radicals to the polymer. These free radicals can be added either through heat, light or in the form of peroxide catalysts or promoters and similar reactive systems. Selection of the R group additionally is made through a consideration of polymer used in the composite. Thermosetting polymers can be used to chemically bond the silane to the polymer phase if a thermoset polymer is selected. The reactive groups in the thermoset can include methacrylyl, styryl, or other unsaturated or organic materials. Thermoplastic materials with reactive sites can be used to increase the reactivity between the polymer phase and the metal particulate. Such thermoplastics having reactive sites in either the backbone or groups pendant to the polymer backbone include polyvinylchloride, polyphenylene sulfite, acrylic homopolymers, maleic anhydride containing polymers, acrylic materials, vinyl acetate polymers, diene containing copolymers such as 1,3-butadiene, 1,4-pentadiene, halogen or chlorosulfonyl modified polymers or other polymers that can react with the composite systems of the invention. Condensation polymeric thermoplastics can be used including polyamides, polyesters, polycarbonates, fluoropolymers, polysulfones and similar polymer materials by reacting end groups with silanes having aminoalkyl, chloroalkyl, isocyanato or similar functional groups. Polyolefin materials including polyethylene and polypropylene can be coupled to the metal particulate using silanes such as alkyl silanes or amino silanes having a substantial aliphatic substituent. Chemical bonding to polyethylene can be achieved using a vinyl silane and reacting the metal particulate with the vinyl silane followed by compounding the modified metal particulate with the polymer phase in the presence of a peroxide catalyst or promoter such as dicumyl peroxide or bis(t-butylperoxy) materials. Chemical bonding to polypropylene or a polyethylene can be achieved when the reactive materials of sulfonyl azide compound. The filler is reacted with a silylsosulfonylazide and then combined with the polymer at an elevated temperature.

The polymer material preferably has a polarity that is matches the interfacial modifier. The interfacial modifier material is selected such that it is a material that associates with the metal particle surface and presents a surface that is compatible with the polymer filling the excluded volume.

Titanate or zirconate coupling agents can be used. Such agents have the following formula:

$$(RO)_m-Ti-(O-X-R'-Y)_n$$

$$(RO)_m-Zr-(O-X-R'-Y)_n$$

wherein titanate chemistries provide superior bonds to transition metals and the lanthanide series. Titanates provide antioxidant properties and can modify or control cure chemistry. Zirconate provides excellent bond strength but maximizes curing, reduces formation of off color in formulated thermoplastic materials. A useful zirconate material is neopentyl (diallyl)oxy-tri(dioctyl)phosphato-zirconate.

The metal polymer composites of the invention can be used in a variety of embodiments including projectiles, high density sheeting with attachment means such as adherent coatings, fishing lures, fishing weights, automobile weights, vehicle tire wheel weights with attachment clips, radiation shielding, golf club components, sporting equipment, gyroscopic ballast, cellular phone vibrating weights or laboratory weight noise and vibration barriers, or other embodiments that require high density material with varying combinations of moldability, ductility, and dimensional stability.

The high density materials of the present invention and all its embodiments are suitable for numerous processing methods. Selection of processing methods and formulation of base materials can be based upon required end use product requirements. The following examples illustrate this point.

An embodiment of the present invention is a flexible or malleable composite that could be used in projectiles including shot gun pellets and other ammunition, stents for heart or artery applications, radiation shielding garments, or extruded and coextruded line for multiple applications including string line and fishing line. An example composite with these characteristics might include a combination of tungsten, a fluoropolymer as the binder, and a zirconate interfacial modifier. The end use product could be the result of an extrusion or injection molded part.

Yet another embodiment of the present invention is a high output production, high density composite that could be used in fishing lures or weights with or without the optionally included interfacial modifier, or cellular phone shielding or internal vibratory mechanisms. An example composite with these characteristics might include a combination of tungsten, polyvinyl chloride as the binder, and an alkaline metal stearate or a stearate amide interfacial modifier. The end use product could be the result of an extrusion or injection molded part.

Yet another embodiment of the present invention is a high output production, high density composite that could be used in fishing lures or weights with or without the optionally included interfacial modifier, or cellular phone shielding or internal vibratory mechanisms. An example composite with these characteristics mi t include a combination of tungsten. polyvinyl chloride as the binder, and an alkaline metal stearate or a stearate amide interfacial modifier as one extrudate in a coextrusion operation, the second extrudate including a second composite or a thermoplastic or thermoset polymer. The composite articles formed by coextrusion are layered sheets, flat articles, or other multilayer articles shaped by passing the coextrudate through a shaped die.

Yet another embodiment of the present invention is a low output production, high cure time, and high density composite that could be used in automobile or truck pneumatic tire wheel weights or other ballasts, or other products that could be produced in bulk forms. An example composite with these characteristics might include a combination of tungsten, polyester as the binder, and a zirconate interfacial modifier. The end use product could be the result of injection molding, or bulk molding parts.

Yet another embodiment of the present invention is a high output production, high density composite that could be used for fishing lures and vehicle pneumatic tire wheel weights, crankshaft and driveshaft weights and aircraft balancing weights. An example composite with these characteristics might include a combination of tungsten, polystyrene as a binder and a zirconate interfacial modifier. The end use product could be the result of injection molding, or bulk molding parts.

In addition to the aforementioned illustrative embodiments, additional processing methods are, but not limited to; Injection, compression molding, thermoset and thermoplastic extrusion, centrifugal molding, rotational molding, blow molding, casting, calendaring, liquid fill thermoset molding or filament winding to form a variety of shapes in conjunction with sequential compounding.

Yet another embodiment of the invention includes colorization of the resulting composites where color is important for identification or as dictated by the end use requirements. Color additives are typically less than 1% of the resulting composite by weight and volume fraction.

Composition and Manufacture

In the manufacture of the composite of the invention, the metal polymer particle size and shape distribution must be selected to obtain packing characteristics, combined with the appropriate polymer and then extruded at appropriate conditions. During the blending step, the metal particulate and the polymer are intimately mixed. The interfacial modifier is commonly added to the blended material or can be added to the metal particulate before combining the modified metal with the polymeric material. As discussed above, many of the fluorocarbon materials require no interfacial modification and are compatible with the metal particulates. Solvent blending can be used to introduce the polymer and metal particulate if necessary.

The blended composite material can then be extruded under conditions of shear, temperature and time to obtain maximized density and other composite polymeric characteristics. The preferred equipment for mixing and extruding the composition is an industrial extruder device such as those obtainable from Brabender or Cincinnati Millicron. Once the materials are mixed under appropriate conditions of shear, temperature and time, the properties of the composite are maximized in density, storage modulus, etc. The resulting polymer material can be extruded in the form of a pellet, chip or other raw material for further processing or can be extruded into a finally useful shape. In a preferred mode, the metal particulate, preferably containing a interfacial modifying material, is placed in a volumetric hopper to proportion the particulate into the extruder. The polymer material is similarly input into the system. The amounts of particulate and polymer are gauged to ensure the composite material contains the appropriate proportions on a weight or preferably volumetric basis. Commonly, the material is blended on input and introduced into an extrusion device, preferably a single or twin screw extruder. Such a device typically has a mixing section, a transport section and a melt section. Each section has a desired heat profile resulting in appropriate blending and interfacial modification. The following example was performed to illustrate the invention in extruded composite materials. The following information illustrates the typical condition and composite composition.

The high density metal polymer composite materials having the desired physical properties can be manufactured as follows. In a preferred mode, the surface of the metal particulate is initially prepared, the interfacial modifier is reacted with the prepared particle material, and the resulting product is isolated and then combined with the continuous polymer phase to affect a reaction between the metal particulate and the polymer. Once the composite material is prepared, it is then formed into the desired shape of the end use material. Solution processing is an alternative that provides solvent recovery during materials processing. The materials can also be dry-blended without solvent. Blending systems such as ribbon blenders obtained from Drais Systems, high intensity dry blenders available from Littleford Brothers and Henschel are possible. Further melt blending using Banbury, Farrell single screw or twin screw compounders is also useful. When the materials are processed as a plastisol, organosol or latex with solvent, liquid ingredients are generally charged to a processing unit first, followed by polymer, metal particulate and rapid agitation. Once all materials are added a vacuum can be applied to remove residual air and solvent and liquids the mixing is continued until the product is uniform and high in density with good mechanical properties.

Dry blending is useful due to advantages in cost, however certain embodiments can be compositionally unstable due to differences in particle size. In dry blending processes, the composite can be made by first introducing the polymer, combining the polymer stabilizers, if necessary, at a temperature from about ambient to about 60° C. with the polymer, blending a metal particulate (modified if necessary) with the stabilized polymer, blending other process aids, colorants, indicators or lubricants followed by mixing in hot mix transfer to storage, packaging or end use manufacture.

Interfacially modified materials can be made with solvent techniques that use an effective amount of solvent to initiate formation of a composite. When interfacially modification is substantially complete, the solvent can be stripped. Such solvent processes are conducted as follows:

1) Solvating the interfacial modifier or polymer or both;
2) Mixing the metal particulate with interfacial modifier into a bulk phase or polymer master batch: and
3) Devolatilizing the composition in the presence of heat & vacuum above the Tg of the polymer When compounding with twin screw compounders or extruders, a preferred process can be used involving twin screw compounding as follows.

1. Add metal particulate and raise temperature to remove surface water (barrel 1).
2. Add interfacial modifier to twin screw when metal particulate is at temperature (barrel 3).
3. Disperse/distribute interfacial modifier on metal particulate.
4. Maintain reaction temperature to completion.
5. Vent reaction by-products (barrel 6).
6. Add polymer (barrel 7).
7. Compress/melt polymer.
8. Disperse/distribute polymer in particulate.
9. React modified particulate with polymer binder.
10. Vacuum degas remaining reaction products (barrel 9).
11. Compress resulting composite.
12. Form desired shape, pellet, lineal, tube, injection mold article, etc. through a die or post-manufacturing step.

Alternatively in formulations containing small volumes of continuous phase:

1. Add polymer.
2. Add interfacial modifier to twin screw when polymer is at temperature.

3. Disperse/distribute interfacial modifier in polymer.

4. Add metal particulate and disperse/distribute particulate.

5 Raise temperature to reaction temperature.

6. Maintain reaction temperature to completion.

7. Compress resulting composite.

8. Form desired shape, pellet, lineal, tube, injection mold article, etc. through a die or post-manufacturing step.

Alternatively in formulations for presized materials:

1. Add polymer.

2. Raise the temperature of the polymer to a melt state

3. Add metal particulate which has been pre-treated with the interfacial modifier and disperse/distribute particulate.

4. Compress resulting composite.

5. Form desired shape, pellet, lineal, tube, injection mold article, etc. through a die or post-manufacturing step.

Certain selections of polymers and particulates may permit the omission of the interfacial modifiers and their related processing steps.

Compounding Process Summary—Methodology

Multiple continuous compounding trials were conducted with the tungsten composite material similar to Example 8. The following section details the parallel, co-rotating, twin-screw compounding technology employed during the trials.

Sequencing of the necessary unit operations must accomplish complete polymer matrix mastification and distribution of the interfacial modifier, prior to the introduction of metal particulate. Once particulate has been introduced, distributive mixing and devolatilization of the matrix occurs. The devolatilization of the interfacial modifier carrier solution removes solvent. Lastly, pressurization of the matrix is limited to driving the degree of fill within the twin-screw to 1.

The following extrusion unit operation sequence was agreed upon by the project team as an initial starting point.

1. Polymer feed

2. Dispersive Mixing (Melt processing)

3. Additive Feed (Injection)

4. Distributive Mixing

5. Tungsten Feed

6. Distributive Mixing

7. Vacuum Devolitalization

8. Pressurize

The following equipment list was employed throughout the experimental trials:

ZSK-30 Compounding Extruder

K-Tron Gravimetric Feeding Array & Controller

Zenith Gear Pump with Injection Nozzle

Strand Pelletizing System

All equipment was verified for accuracy. Particular attention was paid to the verification of the liquid injection system. This was performed to ensure proper dilution of the interfacial modifier within a carrier solvent.

The typical output of the unit is 200 lbs./hr.

In summary, the present invention, as dictated by the specific claims contained herein, represents a breadth of raw material combinations including; metals, polymers, interfacial modifiers, other additives, all with varying particle size distribution, weight fractions, and volume fractions. The present invention also includes a breadth of processing methods, resulting physical and chemical properties, and end-use applications. The following materials exemplify the invention. The materials can all be made into useful composites and shapes.

EXPERIMENTAL

Raw Material Table

| Material | Manufacturer | Location |
| --- | --- | --- |
| THV220A | Dyneon, LLC | Oakdale, MN |
| C-60 Tungsten | Alldyne | Huntsville, AL |
| Technon Plus | Tungsten Heavy Powders, Inc. | San Diego, CA |
| NZ12 | Kenrich Petrochemicals, Inc. | Bayonne, NJ |
| LICA09 | Kenrich Petrochemicals, Inc. | Bayonne, NJ |
| KR238J | Kenrich Petrochemicals, Inc. | Bayonne, NJ |
| SIA0591.0 | Gelest, Inc. | Morrisville, PA |
| 2073 $TiO_2$ | Kronos, Inc. | Cranbury, NJ |
| MEK Peroxide | 3M, Inc. | St. Paul, MN |
| Polyester | 3M, Inc. | St. Paul, MN |
| Polystyrene | Dow Chemical, Inc. | Midland, MI |

Experimental 1

The experiment consisted of four main areas of focus: density, melt flow, tensile strength and elongation. Density measurements were taken by creating samples using an apparatus assembled by Wild River Consulting, which mainly consisted of a metallurgical press fitted with a load cell, and a 3.17 cm cylindrical die modified with a 0.25 cm diameter hole in the bottom of the die. Samples created by these instruments were assumed to be perfectly cylindrical, and therefore measuring the diameter, length, and mass yielded the density of the sample.

During die extrusion, at 1800 kg ram force and 177° C., melt flow was measured for each sample. By timing the sample as it passes the length calibration of the instrument, the rate in which it extruded was calculated. This linear velocity was then normalized by dividing by the orifice radius. The resulting quantity was defined as the melt flow of the material. To ensure complete mixing, extruded materials were re-extruded at least four more times.

The die extruded samples were also tested for tensile elongation. Each sample was trimmed to 10 cm in length, and 1.75 cm from each end was marked. The sample was fixed in the machines grips, where the 1.75 cm marked the point depth the sample was inserted into the grip. The pull to break test was executed, and upon completion the sample was removed.

Two formulations were tested in the experiment using Alldyne C-60 Tungsten and Dyneon THV220A fluoropolymer. The first formulation was designed to achieve a density of 10.8 gm-cm$^{-3}$. The second formulation was designed to achieve the density of 11.4 gm-cm$^{-3}$. Table 1 gives the weight percentages used to create the samples for both formulations. Four interfacial modifiers were tested in the experiment. The first interfacial modifier was a Zirconate coupling agent, NZ 12. The second and third modifiers were Titanate coupling agents, KR238J and LICA 09. The last interfacial modifier was a Silane, SIA0591.0.

TABLE 1

Effect of composite melt flow and mechanical properties with different interfacial modifiers

| Tungsten* | | Fluoropolymer | | Interfacial modifier | Extruded Density g/cc | Melt Flow l/s | Tensile Elongation % | Maximum Stress MPa |
|---|---|---|---|---|---|---|---|---|
| % Weight | % Volume | % Weight | % Volume | | | | | |
| 91.4% | 51.0% | 8.6% | 49.0% | None | 10.2 | 0.4 | 5.9% | 3.6 |
| 91.4% | 51.0% | 8.6% | 49.0% | NZ 12 | 10.1 | 27.5 | 261.7% | 2.4 |
| 91.4% | 51.0% | 8.6% | 49.0% | KR238J | 9.9 | 22.9 | 276.7% | 2.5 |
| 91.4% | 51.0% | 8.6% | 49.0% | LICA 09 | 10.4 | 18.6 | 260.6% | 2.5 |
| 91.4% | 51.0% | 8.6% | 49.0% | SIA0591.0 | 9.9 | 0.2 | 26.8% | 10.5 |
| 92.4% | 54.5% | 7.6% | 45.5% | None | 10.6 | 0.9 | 2.00% | 8.4 |
| 92.4% | 54.5% | 7.6% | 45.5% | NZ 12 | 11.2 | 9.2 | 300.0% | 3.1 |
| 92.4% | 54.5% | 7.6% | 45.5% | KR238J | 11.2 | 7.6 | 290.0% | 4.6 |
| 92.4% | 54.5% | 7.6% | 45.5% | LICA 09 | 11.1 | 4.9 | 225.2% | 2.7 |
| 92.4% | 54.5% | 7.6% | 45.5% | SIA0591.0 | 11.3 | 0.1 | 1.06% | 8.3 |

*With 0.2 wt % interfacial modifier

It was clearly observed that treatment of the tungsten powder caused considerable changes in physical properties. In all formulations, the melt flow was markedly affected with the treatment of an interfacial modifier. The melt flow index of compounded materials increased as much as 68 times the untreated compounds. The effect made can also be observed in the elongation of the material. All four interfacial modifiers caused an increase in tensile elongation, with NZ 12 and KR238J causing the largest changes. Although the materials treated with SIA0591.0 did not exhibit an increase in melt flow, they did exhibit an increase in maximum stress. The SIA0591.0 compounded yielded a maximum stress approximately three fold of a 91.4 wt % tungsten compound without an interfacial modifier. In the case of a fluoropolymer with no interfacial modifier, an elongation of greater than 5% is observed and demonstrates the viscoelastic character of the composite.

Experimental 2, 3, and 4

In tables 2, 3 and 4, the tungsten particulate is first treated with the interfacial modifier. This is done by dissolving the desired amount of the interfacial modifier in a 250 ml beaker containing 50 ml of solvent (usually isopropyl, or some other, alcohol) and then adding 100 grams of tungsten particulate into the beaker. The resulting slurry is then heated at 100° C. until the mixture can no longer be stirred and most of the solvent has been driven off. The beaker containing the tungsten particulate and interfacial modifier is then placed in a forced air oven for 30 minutes at 100° C. The treated tungsten is then added to a 100 ml beaker containing a solution of THV220A dissolved in acetone. The mixture is then heated to 30° C. and continuously stirred until most of the acetone has evaporated. The composite is then placed in a forced air oven for 30 minutes at 100° C. After drying, the composite is pressed in a 3.17 cm cylinder in a metallurgical die at 200° C. and 4.5 metric tons ram force. After 5 minutes, the die is allowed to cool under pressure to 50° C. After releasing the pressure, the composite sample is removed from the die and the physical properties are measured. See Tables 2, 3, and 4 for compositions and properties measured.

THV220A is a polymer of tetrafluoroethylene, hexafluoropropylene, and vinylidene fluoride. NZ 12 is neopentyl (diallyl)oxy-tri(dioctyl)phosphato-zirconate. SIA0591.0 is N-(2-aminoethyl)-3-amonopropyl-trimethoxy-silane. KR 238J is a methacrylamid modified amine adduct available from Kenrich petrochemicals, Bayonne, N.J. LICA 09 is neopentyl(diallyl)oxy-tri(dodecyl)benzene-sulfonyl-titanate.

TABLE 2

Effect of density and mechanical properties in fluoropolymer composite with an interfacial modifier at different concentrations

| Tungsten (19.35 g/ml) | | Thermoplastic (1.90 g/ml) | | Interfacial modifier (NZ 12 - 1.0 g/ml) | | Resulting Composite density (g/cc) | Storage Modulus MPa @ 25° C. |
|---|---|---|---|---|---|---|---|
| % weight | % volume | % weight | % volume | % weight | % volume | | |
| 96.6% | 73.6% | 3.4% | 26.4% | 0.00% | 0.00% | 11.7 | 3856.0 |
| 96.6% | 73.6% | 3.3% | 26.0% | 0.03% | 0.42% | 11.7 | 743.5 |
| 96.7% | 73.6% | 3.1% | 24.3% | 0.14% | 2.09% | 11.7 to 12.2 | 372.4 |
| 97.8% | 73.6% | 0.7% | 5.4% | 1.4% | 21.0% | see note (1) | |
| 96.7% | 73.5% | 3.3% | 25.8% | 0.05% | 0.74% | 12.2 | 711.5 |
| 96.3% | 71.9% | 3.7% | 27.8% | 0.02% | 0.3% | 12.3 | 342.8 |
| 97.9% | 81.9% | 2.1% | 18.0% | 0.01% | 0.10% | 16.2 | see note (2) |

Notes for Table 2:
(1) Crumbled upon removal from the mold
(2) Calculated and Predicted based on current data trend Table 2 shows that there is an effective amount of interfacial modifier. An increase above a stoichiometric surface coverage will then reduce the material properties of the composite (see note 1).

TABLE 3

| Tungsten (19.35 g/ml) | | Thermoplastic (1.40 g/ml) | | Interfacial modifier (NZ 12 - 1.0 g/ml) | | Resulting Composite density (g/cc) | Storage Modulus MPa @ 25° C. |
|---|---|---|---|---|---|---|---|
| % weight | % volume | % weight | % volume | % weight | % volume | | |
| Effect of density and mechanical properties on PVC polymers with the interfacial modifier NZ 12 Thermoplastics (PVC) | | | | | | | |
| 97.4% | 73.1% | 2.6% | 27.0% | 0.00% | 0.00% | 11.6 | 4407.0 |
| 97.4% | 73.1% | 2.6% | 26.5% | 0.03% | 0.4% | 11.7 | 3564.0 |
| 97.5% | 73.1% | 2.4% | 24.8% | 0.1% | 2.0% | 11.9 | 2590.0 |
| 98.0% | 73.5% | 0.5% | 5.6% | 1.4% | 20.9% | | See note (1) |
| Effect of density and mechanical properties on a thermoset polymer with the interfacial modifier NZ 12 Thermosets (Polyester) | | | | | | | |
| 96.6% | 59.6% | 3.4% | 40.0% | 0.04% | 0.4% | 11.7 | 7291.0 |

Note for Table 3:
(1) Crumbled upon removal from the mold

Table 3 shows that multiple thermoplastic and thermoset composites can be made using a select combination of materials and that the degree of properties including density, modulus, elongation can be designed into the materials.

TABLE 4

Effect of density with tungsten with particle size and circularity

| Material | Distribution <min, max> Microns | Roundness (Circularity) Index median | Tungsten* (19.35 g/ml) | | Fluoroelastomer Thermoplastic (1.90 g/ml) | | Resulting Composite density (g/cc) |
|---|---|---|---|---|---|---|---|
| | | | % weight | % volume | % weight | % volume | |
| a | 1.5, 36 | 16.8 | 94.0% | 60.6% | 5.9% | 38.6% | 9.9 |
| b | 10, 130 | 16.4 | 94.0% | 60.6% | 5.9% | 39.0% | 11.5 |
| c | 10, 100 | 15.6 | 96.3% | 71.3% | 3.5% | 26.3% | 11.4 |
| d | 10, 150 | 15.8 | 96.6% | 73.2% | 3.3% | 25.4% | 12.3 |
| e | 15, 150 | 16.0 | 95.4% | 66.9% | 4.6% | 32.8% | 12.4 |
| f | 10, 100 | 16.1 | 93.9% | 60.0% | 6.1% | 39.6% | 11.4 |
| g | 1000, 4000 | 15.8 | 89.4% | 45.3% | 10.6% | 54.6% | 9.8 |

*With 0.03-0.2% NZ 12 interfacial modifier

Table 4 shows that the particle size, distribution and circularity have an impact on the density of the composite. All samples in Table 4 were made such that the formulation would result in the highest density for the resulting composite. Materials d and e have the maximum density due to the presence of both small and large average particle size materials and minimum circularity of about 14. Materials a and g have the lowest density in the table and have either only small or large particulate. The other materials either depart somewhat from the size or circularity parameter (of materials d and e) reducing density.

Experimental 5

The material used for the melt flow experiment data in Table 5 was made as follows. Technon Plus tungsten particulate was modified and blended with the Dyneon THV220A polymer and introduced using a calibrated gravimetric feeder into the extruder. The extruder was a Brabender 1.9 cm single screw with a custom screw, modified to create low compression. The heating zones were set to 175° C., 175° C., 175° C., and 185° C. The screw RPMs were maintained between 20 and 40. The barrel was air-cooled. The material exit speed was about 1 meter per minute. Using the above settings, 92 wt.-% of Technon Plus tungsten pretreated with 0.01 wt.-% of the interfacial modifier Kenrich NZ12, was blended with 8 wt.-% THV220A.

Typical melt flow for the materials of the invention are at least 5 $sec^{-1}$, at least 10 $sec^{-1}$, about 10 to 250 $sec^{-1}$ or about 10 to 500 $sec^{-1}$. In order to measure extrusion melt flow, a custom test system was created. A small hole (0.192 cm in diameter) was drilled into the side of a 3.17 cm metallurgical die. The die was used in conjunction with an instrumented metallurgical press, which allowed monitoring of the die temperature and pressure. With the temperature of the material and pressure of the die set, the material was extruded through the melt flow hole. For a given duration of time, the length of the resulting form was measured, and the results used to determine the peak velocity. With this data, the melt flow was calculated by dividing the velocity difference of the extrudate by the die hole radius.

TABLE 5

The effect of temperature and pressure on melt flow
Material Density 11.2 $gm\text{-}cm^{-3}$ (Fluoroelastomer)

| Melt Flow (l/sec) | Melt Temp (° C.) | Die Pressure (psi) |
|---|---|---|
| 7.8 | 160 | 5700 |
| 60 | 175 | 5700 |
| 220 | 190 | 5700 |

TABLE 5-continued

The effect of temperature and pressure on melt flow
Material Density 11.2 gm-cm$^{-3}$ (Fluoroelastomer)

| Melt Flow (1/sec) | Melt Temp (° C.) | Die Pressure (psi) |
| --- | --- | --- |
| 13 | 175 | 9800 |
| 30 | 180 | 9800 |
| 230 | 190 | 9800 |
| 7.7 | 190 | 2400 |
| 69 | 190 | 5700 |
| 230 | 190 | 9800 |

The results in Table 5 show that the increase in melt temperature at a given pressure demonstrated a melt flow increase as would be seen by a viscoelastic material. Likewise an increase in pressure causes an increase in melt flow, which is again characteristic of a viscoelastic material.

Example Article 1

Article Production

Containing: Polystyrene, Technon Powder, Kronos 2073, and Ken-React NZ12.

Formulation by Weight:

| | |
| --- | --- |
| Polystyrene | 0.6563 g |
| Technon Plus tungsten particulate | 12.1318 g |
| Kronos 2073 TiO2 particulate | 0.14719 g |
| Ken-React NZ 12 | 0.2740 g |

Polystyrene was dissolved in a blend of toluene, MEK and acetone to a total solid of 38 wt.-%. The two particulates were dispersed with stirring in the same solvent blend and the NZ 12 was added to this dispersion. After stirring to break the TiO2 agglomerations the Polystyrene solution was added and stirred while blowing off the solvent till the blend became a semisolid. This material was then compression molded into a jig with No. 1 hook.

Example Article 2

Containing: Polystyrene, Technon Powder, and Ken-React NZ12.

Formulation by Weight:

| | |
| --- | --- |
| Polystyrene | 0.6011 g |
| Technon Plus tungsten particulate | 12.0927 g |
| Ken-React NZ 12 | 0.03 g* |

Polystyrene was dissolved in a blend of toluene, MEK and acetone to a total solid of 38 wt.-%. The tungsten particulate was dispersed with stirring in the same solvent blend and the NZ12 was added to this dispersion. The polystyrene solution was added and stirred while blowing off the solvent till the blend became a semisolid. This material was then compression molded into a slip sinker.

Example Article 3

Containing: Polyester Polymer, Technon Powder, Kronos 2073 TiO2, and Ken-React NZ12.

Formulation by Weight:

| | |
| --- | --- |
| Polyester Polymer | 0.4621 g |
| Technon Plus tungsten particulate | 13.0287 g |
| Kronos 2073 TiO$_2$ particulate | 1.5571 g |
| Ken-React NZ 12 | 0.0366 g |
| MEK peroxide | |

Polyester Polymer was added to the tungsten, and TiO2 particulate. Acetone was added to aid in the dispersion of the NZ12. After the blend started to show signs of color development i.e. TiO2 dispersion more acetone was added and then the MEK peroxide. This material was compression molded into a slip sinker.

Example Article 4

Containing: Polyester Polymer, Technon Powder, Kronos 2073 TiO2, and Ken-React NZ12.

Formulation by Weight:

| | |
| --- | --- |
| Polyester Polymer 3M | 1.6000 g |
| Technon Plus tungsten particulate | 36.3522 g |
| Kronos 2073 TiO2 particulate | 4.8480 g |
| Ken-React NZ12 | 0.0400 g |
| MEK peroxide | |

Polyester Polymer was added to the tungsten, and TiO2 particulate. Acetone was added to aid in the dispersion of the NZ12. After the blend started to show signs of color development i.e. TiO2 dispersion more acetone was added and then the MEK peroxide. This material was compression molded into the No. 1 slip sinker.

Example Article 5

Containing: Fluoroelastomer, Technon Particulate, and Ken-React NZ 12.

Formulation by Weight:

| | |
| --- | --- |
| Fluoroelastomer THV220A Dyneon | 1.6535 g |
| Technon Plus tungsten particulate | 36.8909 g |
| Ken-React NZ 12 | 0.0400 g |

The NZ 12 was blended into the tungsten particulate with the aid of acetone. The THV220A was dissolved in acetone to 38 wt.-% and then added to the tungsten slurry. This blend was stirred until the solvent is removed and only the polymer blend remains and then the material is compression molded in a 3.17 cm metallurgical press. This large pellet was diced and oven dried at 104° C. to dryness then reformed in a metallurgical press at 5700 lb-in$^{-2}$ and 177° C. Density of this material was 11.7 gm-cm$^{-3}$.

RESULTS

Samples similar to the formulae above prepared using pentanol solvent and modifier for treatment solvent.

|  | Pre-treat Temp (C.) | Extruded Density (g/cc) | Shear Rate (l/s) | Tensile Elongation (%) |
|---|---|---|---|---|
| Pentanol |  |  |  |  |
| Sample 1 | 80 | 10.0854 | 2.3415 | 243.75% |
| Sample 2 | 135 | 8.1879 | 5.3610 | 175.00% |
| Isopropanol |  |  |  |  |
| Sample 3 | 80 | 10.5398 | 0.5703 | 225.00% |
| Sample 4 | 135 | 9.9231 | 0.4027 | 153.03% |

The series are named for the solvent used in compatibilizing. Predicted refers to the predicted elongation if Solvent-Exchange limited.

Data from Pentanol-Compatibilized Material

Sample 1—Temperature 80° C.

| Shear Rate | | |
|---|---|---|
| Run 1 | 2.2976 | |
| Run 2 | 2.2164 | |
| Run 3 | 2.5106 | |
| Average | 2.3415 | |
| Density | | |
| Stick 1 | 10.0367 | |
| Stick 2 | 10.0406 | |
| Stick 3 | 10.1788 | |
| Average | 10.0854 | |
| Elongation | Pentanol | Isopropanol |
| 80 | 243.75% | 225.00% |

Sample 2—Temperature 135° C.

| Shear Rate | | |
|---|---|---|
| Run 1 | 5.2428 | low temp |
| Run 2 | 4.2487 | low temp |
| Run 3 | 6.5916 | at temp |
| Average | 5.3610 | |
| Density | | |
| Stick 1 | 8.1621 | Average |
| Stick 2 | 8.1939 | RelStdDev |
| Stick 3 | 8.2078 | |
| Average | 8.1879 | |
| Elongation | Pentanol | Isopropanol |
| 135 | 175.00% | 153.03% |

Pertinent Physical Properties of Materials used in Experiment

|  | Boiling/Melting (° C.) | Density (g/cc) |
|---|---|---|
| 2-propanol (l) | 82.4 | 0.785 |
| n-pentanol (l) | 137.0 | 0.811 |
| Acetone (l) | 56.2 | 0.7857 |
| NZ12 | 104.4 | 1.06 |
| THV220A (s) | 110.0 | 1.9 |
| Taegutec (s) | 3683.2 | 18.4 |

The analysis of elongation data showed that there was a strong correlation to temperature. Regardless of solvent, the elongation of extruded material was approximately 225% at 80° C. and 175% at 135° C. A small increase in elongation was observed in materials compatibilized using pentanol, and the increase was consistent for both temperatures. This increase yielded an elongation of 175%, still far less than the predicted value of 225%. These observations conclude that the limiting mechanism for the coupling reaction is not solvent-exchange, and that a mechanism within the coupling agent is limited by temperature dependence.

DETAILED DESCRIPTION OF THE DRAWINGS

FIG. 1 shows an isometric view of a stent comprising a metal polymer composite of the invention. The stent can be extruded in a circular hollow cross section and can be carved with known mechanical or laser methods from the extruded tube of the composite. The stent can be also directly molded into the form shown. The stent 10 can comprise the composite and have flexible members 11 that permit expansion upon placement in a vascular lumen. The stent has curved members 13 and linear members 12 that can be formed from the composite by direct molding techniques or by carving the structures from a molded tube.

The usefulness of the extrudable material that can have viscoelastic properties is illustrated by the following Figures. In the Figures, extruded objects are exemplified which can be used in a cooperative mode. In each of the Figures, cooperative shapes are formed that can interact and interlock to form a stable mechanical structure. The flexibility of the overall structure, along with the flexibility of the inserts and recesses, render the extruded structures usable in their intended role.

Figure 2A:
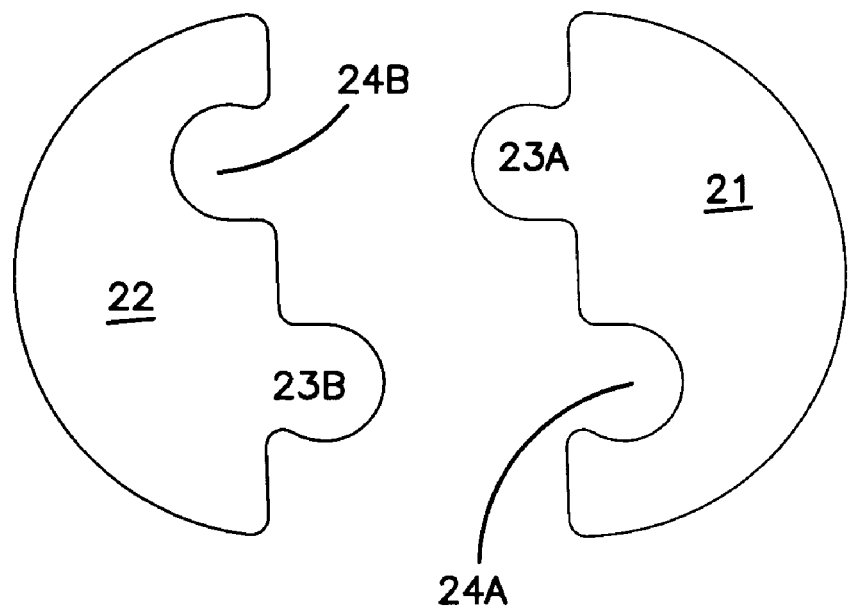
FIGS. 2-4 are extruded structures having interlocking members that cooperate to form an open and a closed aspect.
Figure 2B:
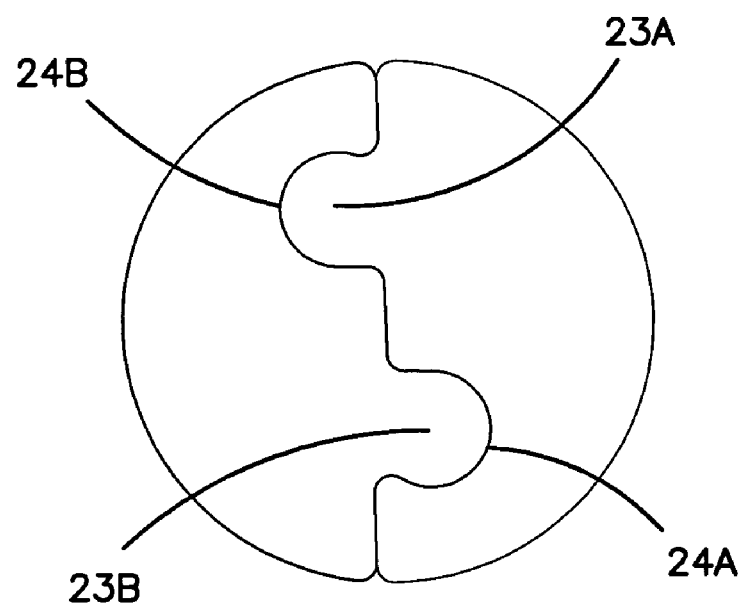

FIG. 2A shows an extruded member having a symmetrical aspect. The extruded object 20 has a body 21 with an insert 23A and a symmetrical recess 24A. Such a structure 20 can be extruded and cut to length and then each length can be mated with a symmetrical member such that insert 23A can be inserted into recess 24B simultaneously with the insertion of insert 23B into recess 24A to interlock body 21 with body 22 to form a fixed mechanically stable assembly. That assembly is shown in FIG. 2B. In FIG. 2A, an object is formed which is substantially entirely filled throughout the combined body.

Figure 3A:
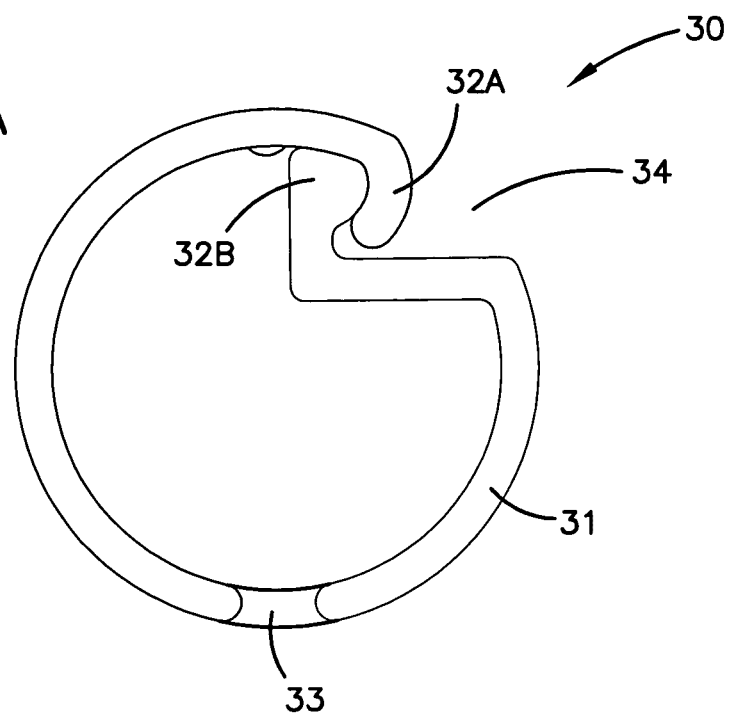
Figure 3B:
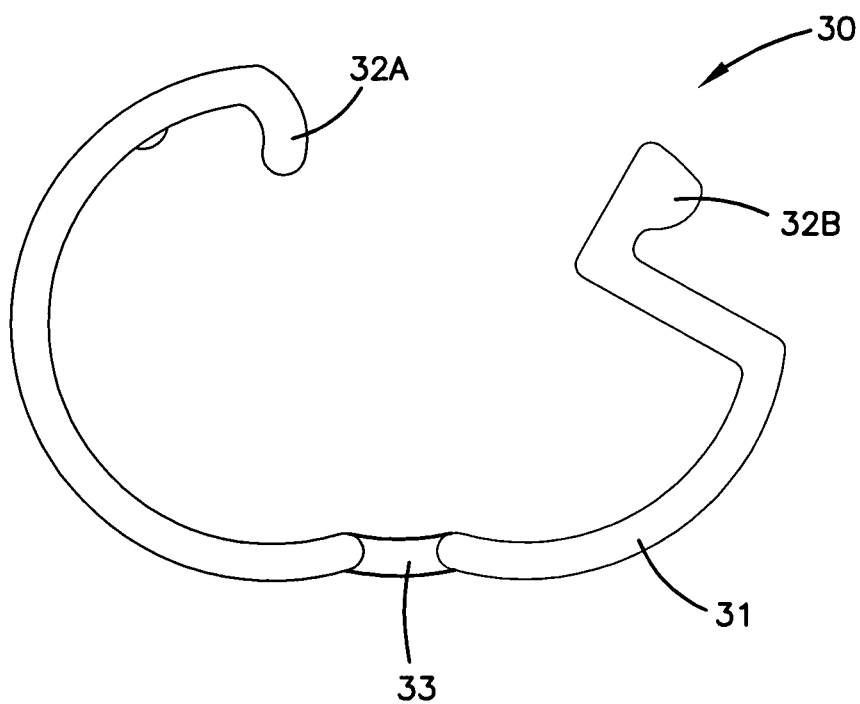

The invention can additionally be embodied in a flexible hollow member that can be joined using interlocking tabs formed by extrusion. In FIG. 3A, a substantially circular extrudate is shown in cross-section. FIG. 3A shows the structure after extrusion prior to post-extrusion processing into a flexible useful unit. The unit 30 shows a body 31, a co-extruded but flexible hinge 33, a first interlocking tab 32A and a cooperative second interlocking tab 32B in the extruded unit. A removable portion 34 can be pulled, cut or otherwise removed from the extruded portion 30 to permit the effective opening and closing of the circular extrudate using the cooperating tabs 32A and 32B. Depending on the degree of flexibility, the optional hinge 33 can be co-extruded with known extrusion technologies to form a flexible hinge with the high density extrudable material in body 31. Extrudable hinge 33 can comprise typical elastomeric materials including the fluoropolymers of the composite, but also can include typical rubbery polymeric materials such as poly-isobutylenes, ABA block copolymers and other well known rubbers or flexible polymeric materials.

Figure 4A:
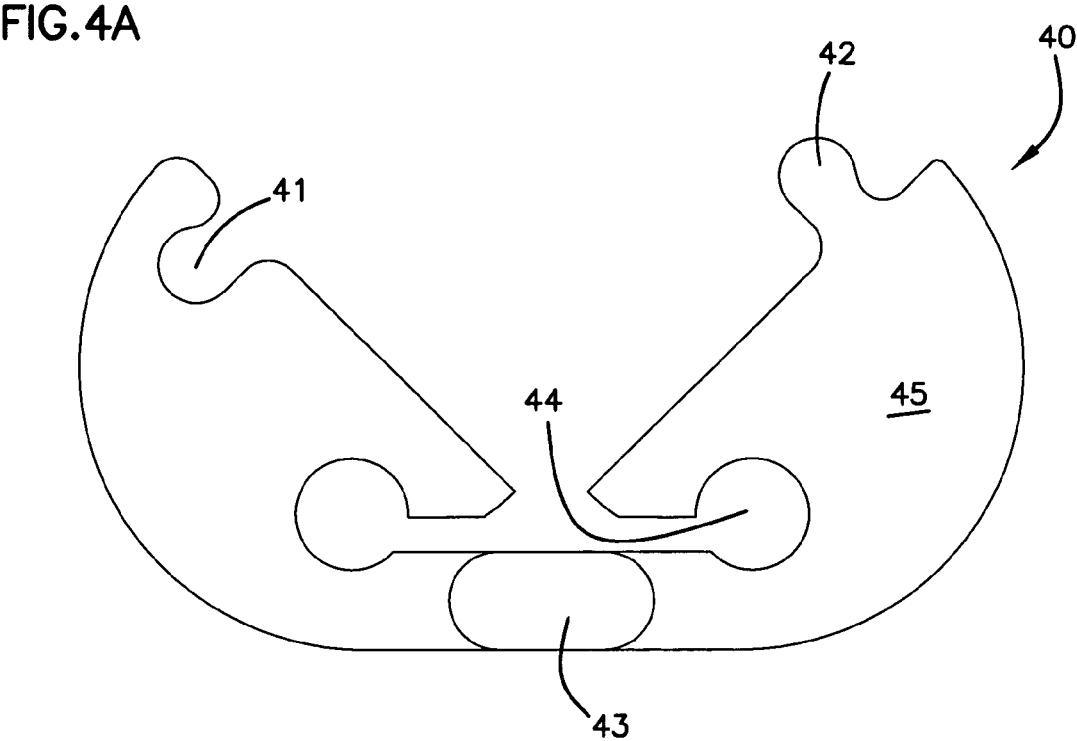
Figure 4B:
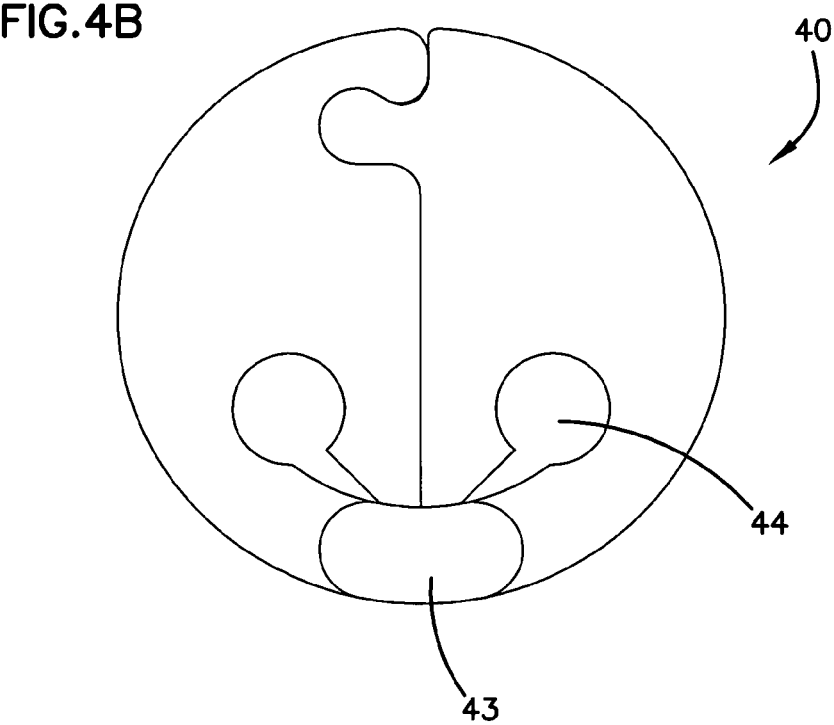

FIGS. 4 and 4A show additional extruded member on cross-section that can be used to form a useful structure of the invention. In FIG. 4A, the structure can be extruded with an extrudate 40, a body 45. Body 45 includes flexible insert 42 and flexible aperture 41 that can cooperate to press fit form a useful interlocking joint. The body 45 additionally comprises a flexible hinge portion 43 that can comprise a flexible hinge as disclosed above. The body also is formed using apertures 44 which can remain within the substantially solid joined structure shown in FIG. 4B.

Figure 5:
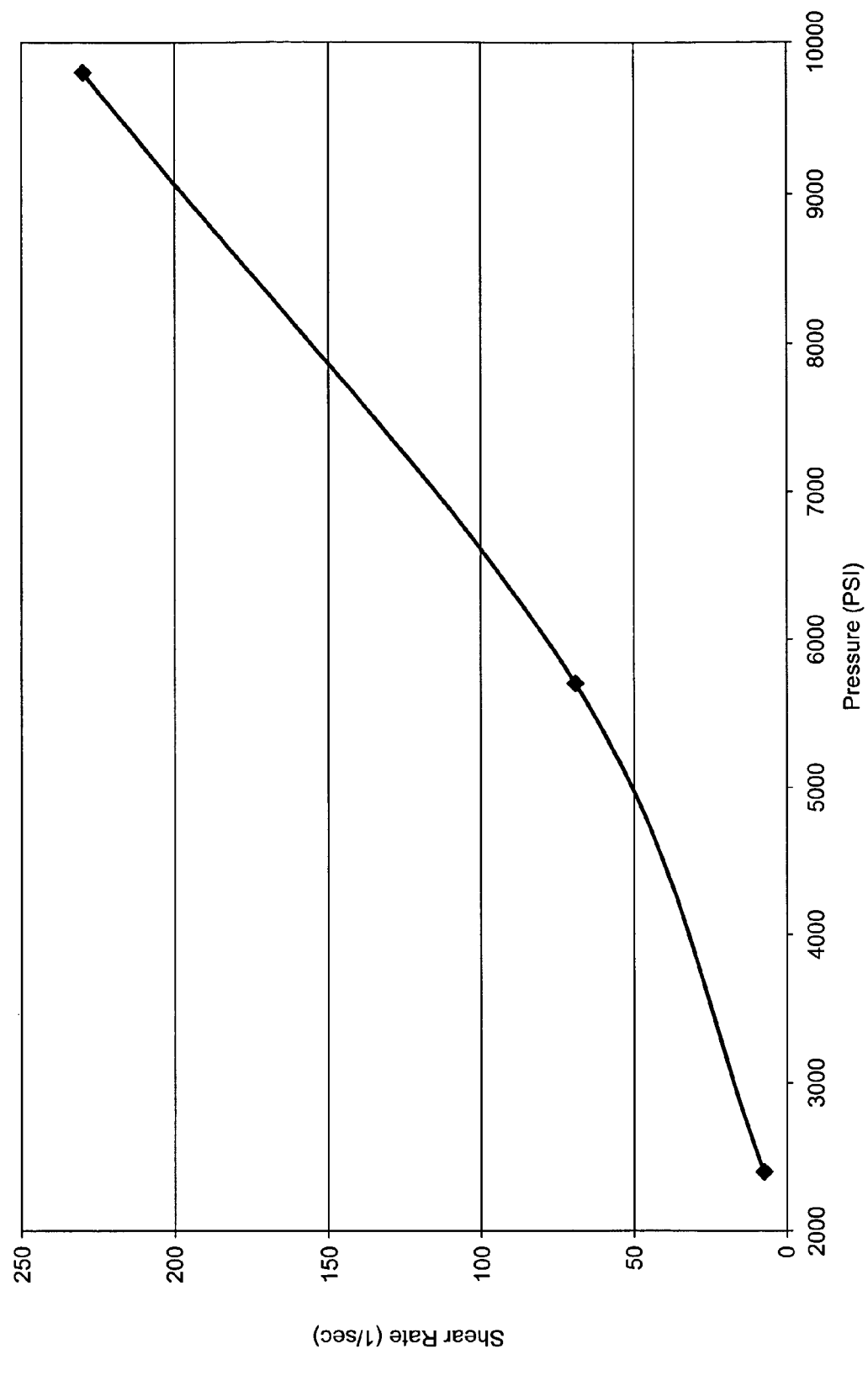
FIGS. 5-7 are graphic representations of extrusion data showing the material of the invention can be extruded at useful conditions of rate, temperature and pressure.
Figure 6:
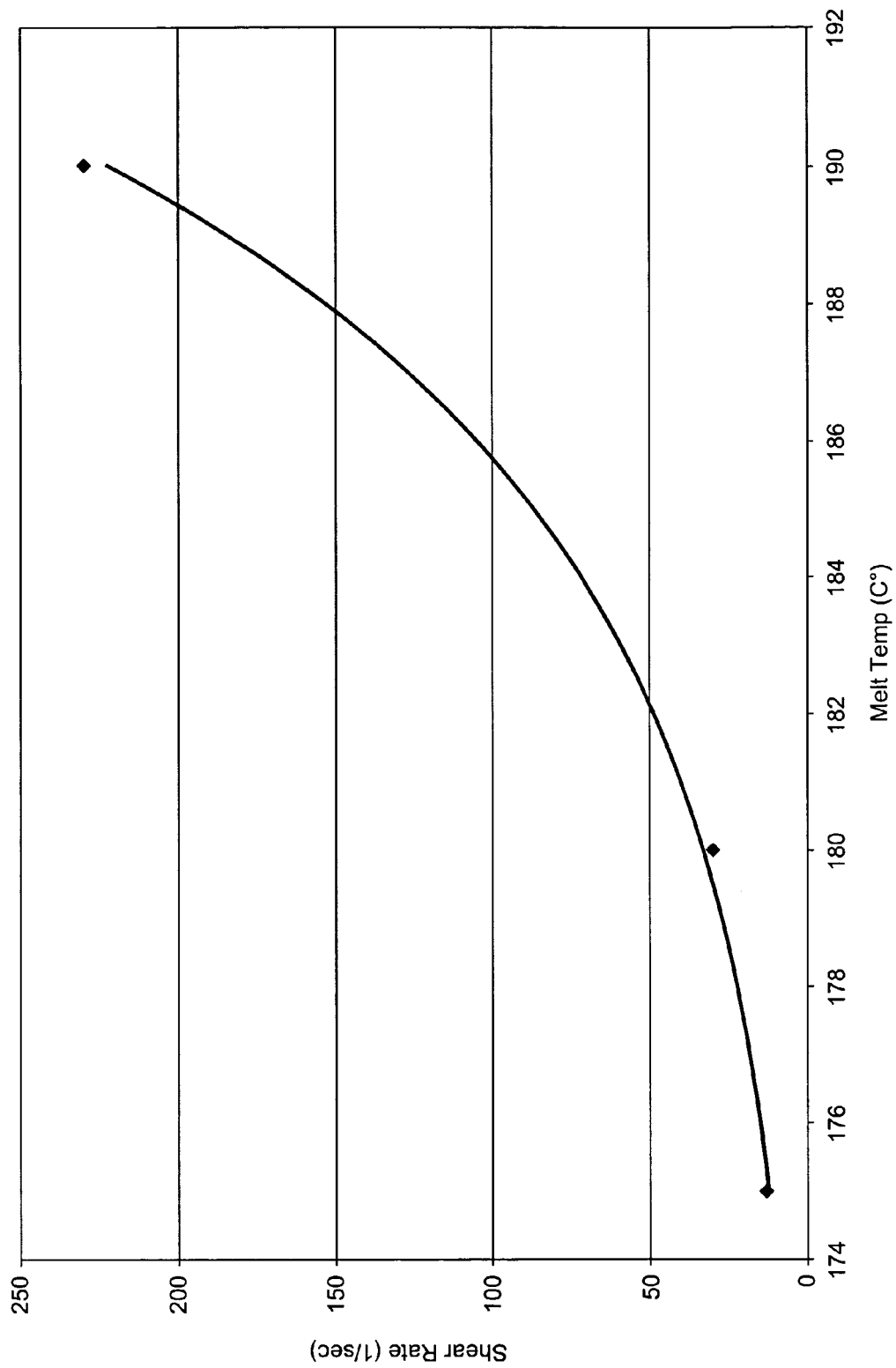
Figure 7:
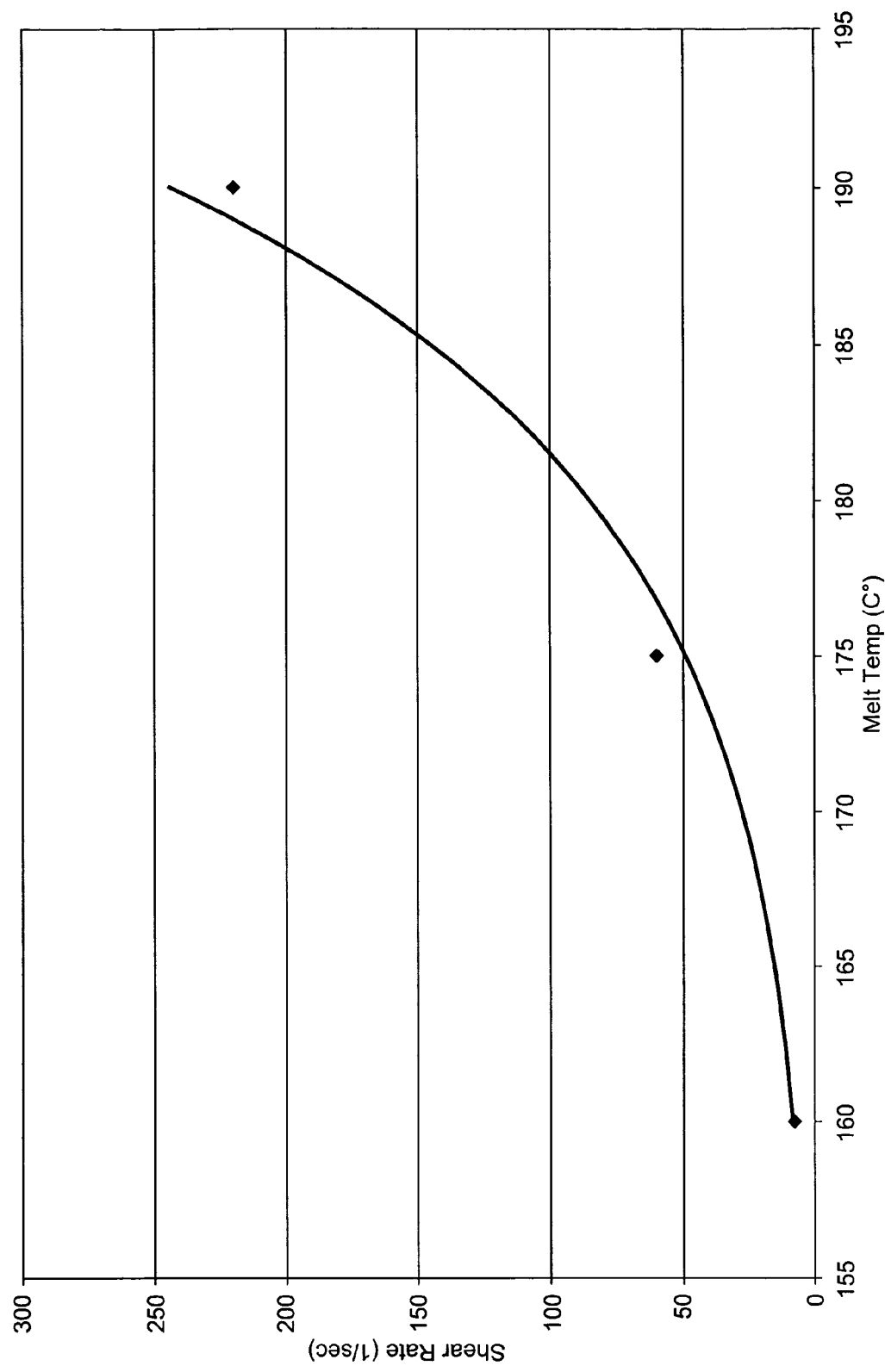

FIGS. 5-7 shows the extrusion performance of the composite of the invention from Example 8 under varied conditions of temperature and pressure showing the material is capable of extrusion at conditions achievable in production equipment.

The above specification, examples and data provide a complete description of the manufacture and use of the invention as known. As many embodiments of the invention can be made without departing from the spirit and scope of the invention, the invention resides in the claims hereinafter appended.

I claim:

1. A method to extrude a metal polymer composite, the composite comprising a metal particulate phase and a polymer phase, the method comprising:
   (a) combining:
      (i) about 96 to 45 volume-% of a metal particulate comprising 5 wt-% or less of particles having a particle size of less than 10 microns, the metal having a density greater than 8 gm-cm$^{-3}$, in a particulate phase having a particle size distribution having at least 10 wt-% of particulate within of about 10 to 70 microns, at least 20 wt-% of the polymer particulate within about 70 to 500 microns, a circularity greater than 13 and an aspect ratio less than 3;
      (ii) about 4 to 53 volume-% of a polymer phase; and
      (iii) about 0.005 to 3 wt-% of an interfacial modifier material to form a composite mix; and
   (b) extruding the composite mixture at a temperature greater than 100° C. and at a shear rate of about 1 to 500 sec$^{-1}$ to form an extruded metal polymer composite; wherein the extruded composite has a density greater than about 7 gm-cm$^{-3}$ and a storage modulus of greater than 300 MPa.

2. The method of claim 1 wherein the extruded metal composite comprises a single polymer source and the interfacial modifier comprises about 0.005 to 0.7 wt-% of the composite.

3. The method of claim 1 wherein the extruded metal composite comprises polymer blend or alloy and the interfacial modifier comprises about 0.005 to 1 wt-% of the composite.

4. The method of claim 1 wherein the metal particulate phase comprises tungsten and the polymer comprises a vinyl polymer.

5. The method of claim 1 wherein the metal particulate phase is present in an amount of about 50 to 85 volume-%.

6. The method of claim 1 wherein the polymer phase is a halogen containing polymer having a density of greater than 1.2 gm-cm$^{-3}$.

7. The method of claim 1 wherein the extruded metal composite comprises a pigment or a dye.

8. The method of claim 1 wherein the metal in the particulate has a density greater than 10 gm-cm$^{-3}$.

9. The method of claim 1 comprising extruding the composite mixture at a temperature greater than 180° C. and at a shear rate of about 5 to 500 sec$^{-1}$.

10. An injection molding process comprising heating a composite to an elevated temperature and injecting that composite into a mold; wherein the composite comprises a polymer, and a metal particulate coated with an interfacial modifier, with the metal of the particulate having a density greater than 4 gm-cm$^{-3}$ and the interfacial modifier being in an amount between 0.005 and 1 wt-%.

11. A compression molding process comprising molding a composite under elevated pressure; wherein the composite comprises a polymer, and metal particulate coated with an interfacial modifier, with the metal of the particulate having a density greater than 4 gm-cm$^{-3}$ and the interfacial modifier being in an amount between 0.005 and 1 wt-%.

12. A sequential compounding process comprising blending a polymer and metal particulate coated with an interfacial modifier, with the metal of the particulate having a density greater than 4gm-cm$^{-3}$ and the interfacial modifier being in an amount between 0.005 and 1 wt-%.

13. A sequential compounding process comprising
   a first operation of blending a substantially solvent-free mixture of a polymer and metal particulate coated with an interfacial modifier, with the metal of the particulate having a density greater than 4 gm-cm$^{-3}$ and the interfacial modifier being in an amount between 0.005 and 1 wt-%, to form a composite, and
   a second operation of extruding or molding an object, wherein the molding is compression molding or injection molding.

14. A sequential compounding process comprising
   a first operation of blending solvent, polymer, and metal particulate coated with an interfacial modifier, with the metal of the particulate having a density greater than 4 gm-cm$^{-3}$ and the interfacial modifier being in an amount between 0.005 and 1 wt-%, and a second operation of extruding or molding an object, wherein the molding is compression molding or injection molding.

15. The method of claim 14 wherein the object is formed by wetting the metal particulate with solvent and removing the solvent after processing.

16. A sequential compounding process comprising
   blending solvent, polymer, and metal particulate coated with an interfacial modifier, with the metal having a density greater than 7 gm-cm$^{-3}$ and the interfacial modifier being in an amount between 0.005 and 1 wt-%, followed by a solvent degassing of the composite during the melt portion of mixing.

17. A method of manufacturing a metal polymer composite article comprising:
   (a) forming a metal polymer mixture by combining:
      (i) a metal particulate, the metal having a density greater than 4 gm-cm$^{-3}$ and an excluded volume of about 13 to about 60 volume-%, the metal particulate comprising a coating of an effective composite forming amount of an interfacial modifier; and
      (ii) a polymer phase comprising a polymer in an amount sufficient to substantially occupy excluded volume of the particulate;

(b) blending the metal polymer mixture to form a metal polymer composite blend having a density greater than about 4 gm-cm$^{-3}$ and a storage modulus of greater than 300 MPa; and (c) shaping the metal polymer composite blend to form a metal polymer composite article.

18. The method of claim 17 wherein the article comprises about 0.005 to 3 wt.-% of the interfacial modifier.

19. The method of claim 17 wherein the polymer is a halogen containing polymer having a density of greater than 1.2 gm-cm$^{-3}$.

20. The method of claim 17 wherein the article comprises a pigment or a dye.

21. The method of claim 17 wherein the metal particulate comprises at least 5 wt.-% of the metal with particle size ranging greater than 250 microns.

22. The method of claim 19 wherein the polymer comprises a fluoroelastomer.

23. The method of claim 22 comprising shaping by extruding the mixture at a temperature greater than 180° C. and at a shear rate of about 5 to 500 sec$^{-1}$.

24. The method of claim 17, further comprising extruding the blend with a coextrudate comprising a polymer.

25. The method of claim 17, further comprising passing the blend through a shaped die to form a shaped composite.

26. The method of claim 25, wherein the shaped die comprises a shape that forms two shaped composite articles to interlock when pressed together.

27. The method of claim 17 wherein the metal particulate comprises a particle size of greater than 10 microns.

28. The method of claim 17 wherein the blending is performed in an extruder.

29. The method of claim 28 wherein at least 5 wt.-% of the metal particulate comprises a particle size of 10 to 70 microns and at least 5 wt.-% of the metal particulate comprises a particle size of 70 to 250 microns.

30. The method of claim 28 wherein said shaping comprises extruding at a temperature greater than 100° C. and at a shear rate of about 1 to 500 sec$^{-1}$.

31. The method of claim 30 comprising shaping the composite article by extruding the metal polymer mixture at a temperature greater than 150° C. and at a shear rate of about 10 to 300 sec$^{-1}$.

32. The method of claim 31, where the composite article has significantly reduced wear characteristics.

33. A method of manufacturing a metal polymer composite article comprising:

(a) forming a metal polymer mixture by combining:
 (i) a metal particulate comprising stainless steel, the steel having a density greater than 4 gm-cm$^{-3}$ and an excluded volume of about 13 to about 60 volume-%, the metal particulate comprising a coating of an effective composite forming amount of an interfacial modifier; and
 (ii) a polymer phase comprising a thermoplastic polymer in an amount sufficient to substantially occupy the excluded volume of the particulate;

(b) blending the metal polymer mixture to form a metal polymer composite having a density greater than about 4 gm-cm$^{-3}$ and a storage modulus of greater than 300 MPa; and (c) shaping the metal composite to form a metal polymer composite article.

34. The method of claim 33 wherein the metal particulate comprises stainless steel particles and particles of a second metal.

35. The method of claim 33 comprising shaping the mixture by extruding at a temperature greater than 100° C. and at a shear rate of about 1 to 500 sec$^{-1}$.

36. The method of claim 33 wherein the composition comprises about 0.005 to 3 wt.-% of the interfacial modifier.

37. The method of claim 35 comprising shaping the mixture by extruding at a temperature greater than 150° C. and at a shear rate of about 10 to 300 sec$^{-1}$.

38. The method of claim 37 comprising extruding the mixture at a temperature greater than 180° C. and at a shear rate of about 5 to 500 sec$^{-1}$.

39. A method of manufacturing a metal polymer composite article comprising:

(a) forming a metal polymer mixture by combining:
 (i) a metal particulate comprising a particle blend of first metal particles and second metal particles, the metal having a density greater than 4 gm-cm$^{-3}$ and an excluded volume of about 13 to about 60 volume-%, the metal particulate comprising a coating of an effective composite forming amount of an interfacial modifier; and
 (ii) a polymer phase comprising a thermoplastic polymer in an amount sufficient to substantially occupy the excluded volume of the particulate;

(b) blending the metal polymer mixture to form a metal polymer composite having a density greater than about 4 gm-cm$^{-3}$ and a storage modulus of greater than 300 MPa; and (c) shaping the metal polymer composite to form a metal polymer composite article.

40. The method of claim 39 wherein the metal particulate comprises a product of separately coating the first metal particles from the second metal particles with interfacial modifier before forming the blend.

41. The method of claim 39 wherein the metal particle composite comprises about 0.005 to 3 wt.-% of the interfacial modifier.

42. The method of claim 39 comprising shaping the metal polymer composite by extruding at a temperature greater than 100° C. and at a shear rate of about 1 to 500 sec$^{-1}$.

* * * * *

UNITED STATES PATENT AND TRADEMARK OFFICE
CERTIFICATE OF CORRECTION

| | | |
|---|---|---|
| PATENT NO. | : 7,491,356 B2 | Page 1 of 1 |
| APPLICATION NO. | : 10/988193 | |
| DATED | : February 17, 2009 | |
| INVENTOR(S) | : Kurt E. Heikkila | |

It is certified that error appears in the above-identified patent and that said Letters Patent is hereby corrected as shown below:

In column 39, line 42, claim 1, replace "polymer" with --metal--

Signed and Sealed this
Twenty-ninth Day of May, 2012

David J. Kappos
*Director of the United States Patent and Trademark Office*